(12) United States Patent
Maruyama et al.

(10) Patent No.: US 7,732,150 B2
(45) Date of Patent: *Jun. 8, 2010

(54) LAMBDOID BACTERIOPHAGE VECTORS FOR EXPRESSION OF FOREIGN PROTEINS

(75) Inventors: Ichiro Maruyama, San Diego, CA (US); Hiroko Maruyama, San Diego, CA (US); Sydney Brenner, Cambridge (GB)

(73) Assignee: The Scripps Research Institute, La Jolla, CA (US)

( * ) Notice: Subject to any disclaimer, the term of this patent is extended or adjusted under 35 U.S.C. 154(b) by 1071 days.

This patent is subject to a terminal disclaimer.

(21) Appl. No.: 11/073,226

(22) Filed: Mar. 3, 2005

(65) Prior Publication Data

US 2006/0030020 A1    Feb. 9, 2006

Related U.S. Application Data

(62) Division of application No. 08/852,020, filed on May 6, 1997, now Pat. No. 6,884,612, which is a division of application No. 08/286,888, filed on Aug. 5, 1994, now Pat. No. 5,627,024.

(51) Int. Cl.
*G01N 33/53* (2006.01)
(52) U.S. Cl. .................. 435/7.2; 435/235.1; 435/320.1; 435/252.33; 530/350
(58) Field of Classification Search ....................... None
See application file for complete search history.

(56) References Cited

U.S. PATENT DOCUMENTS 5,627,024 A * 5/1997 Maruyama et al. ............. 435/5

OTHER PUBLICATIONS

Herman J.C. Berendsen. Science. 1998, vol. 282, pp. 642-643.*
Michael F. Moody. Journal of Molecular Biology 1999, vol. 293, pp. 401-433.*

* cited by examiner

*Primary Examiner*—James S Ketter
(74) *Attorney, Agent, or Firm*—Hugh Wang; Thomas Fitting

(57) ABSTRACT

Lambdoid phage comprising a matrix of proteins encapsulating a genome encoding first and second polypeptides of an autogenously assembling receptor and a receptor comprised of the first and second polypeptides surface-integrated into the matrix via a lambdoid phage tail protein matrix anchor domain fused to at least one of the polypeptides.

24 Claims, 3 Drawing Sheets

λV·mcs

```
        S   S   S   L   D   P   G   P   S   T   N   S                      189
GGGTAGAGCTCAAGCTTGGATCCGGGCCCGTCGACGAATTC                                  9514
    SacI  HindIII                    EcoRI
              BamHI
```

λblue

```
        S   W   P   V   G   P   I   V   T   Q   E   T   A   M   T   M   I   T    195
GGGTAGAGCTGGCCTGTTGGGCCAATTGTCACACAGGAAACAGCTATGACCATGATTACG                    9533
              SfiI

P   S   L   H   A   C   R   S   T   L   E   D   P   R   V   P   S   S   N   S    215
CCAAGCTTGCATGCCTGCAGGTCGACTCTAGAGGATCCCCGGGTACCGAGCTCGAATTC                       9592
   HindIII                              BamHI           SacI  EcoRI
```

λfoo

```
        S   W   P   V   G   P   T   P   T   P   T   T   P   T   P   T   P   T    195
GGGTAGAGCTGGCCTGTTAGGCCCACTCCGACCCCGACCACTCCCACCCCGACTCCCACC                    9533
              SfiI
  P   T   P   T   P   T   P   T   V   G   P   I   V   T   Q   E   T   A   M   T    215
CCGACCCCGACCCCGACTCCGACCGTTGGGCCAATTGTCACACAGGAAACAGCTATGACC                     9593

M   I   T   P   S   L   H   A   C   R   S   T   L   E   D   P   R   V   P   S    219
ATGATTACGCCAAGCTTGCATGCCTGCAGGTCGACTCTAGAGGATCCCCGGGTACCGAGC                     9653
           HindIII                              BamHI           SacI
  S   N                                                                          221
TCGAATTC                                                                         9661
   EcoRI
```

LAMBDOID BACTERIOPHAGE VECTORS FOR EXPRESSION OF FOREIGN PROTEINS

This application is a divisional of application Ser. No. 08/852,020, filed May 6, 1997, pending, which is a divisional of application Ser. No. 08/286,888, filed Aug. 5, 1994, now issued as U.S. Pat. No. 5,627,024. The disclosures of the foregoing applications are hereby incorporated by reference herein.

TECHNICAL FIELD

The present invention relates to cloning vectors and methods for producing a library of DNA molecules capable of expressing a fusion polypeptide on the surface of a lambdoid phage particle.

BACKGROUND

The expression of polypeptides fused to the surface of filamentous bacteriophage provides a powerful method for recovering a particular sequence from a large ensemble of clones (Smith et al., Science, 228:1315-1517, 1985). Peptides binding to avidin or antibodies have been selected from large libraries by the relatively simple method of panning (Scott et al., Science, 249:386-290, 1990; Devlin et al., Science, 249: 404-406, 1990; and Cwirla et al., Proc. Natl. Acad. Sci. U.S.A., 87:6378-6382, 1990). Larger proteins, such as antibodies (McCafferty et al., Nature, 348:552-554, 1990; Lowman et al., Biochemistry, 30:10832-10838, 1992; and Kang et al., Proc. Natl. Acad. Sci. U.S.A., 88:4363-4366, 1991) and human growth hormone (Bass et al., Proteins, 8:309-314, 1990), have also been fused to surface proteins of filamentous phage which can then be used for the selection of particular sequences from a large number of variants.

In these filamentous phage systems, the foreign protein or polypeptide is fused to the amino-terminus of either coat protein III or coat protein VIII of the filamentous phage M13 and the fused protein is secreted through the *Escherichia coli* cytoplasmic membrane into the periplasmic space. Most of the proteins successfully fused with filamentous phage surface proteins have been secreted proteins and, although Rebar and Pabo (Science, 263:671-673, 1994) have recently used pIII to display three zinc fingers of Zif268 (a DNA-binding protein), many cytoplasmic proteins will interfere with the passage of the fusion product from the cytoplasm to the periplasm.

Furthermore, cDNA gene products cannot be directly expressed as fusion proteins to the amino-terminus of the viral coat proteins due to transcriptional stop sites present at the 3' end of non-translated regions in eukaryotic cDNA obtained by poly($A^+$) selection of mRNA followed by poly (A) priming (*Molecular Cloning: A Laboratory Manual, Second Edition*, Maniatis et al., eds., Cold Spring Harbor, N.Y., 1989). These facts prevent the use of filamentous phage systems developed thus far for cDNA library screening.

Herein described is a lambda vector system useful for the expression of a foreign protein on its surface which should be more appropriate for proteins that fold in the cytoplasm. The lambda vector of this invention could therefore complement the filamentous phage system in the identification of novel polypeptides with a biological activity.

BRIEF SUMMARY OF THE INVENTION

A new surface-integration technology has been discovered for expressing a cytoplasmic recombinant gene product on the surface of a lambdoid phage containing the recombinant gene. The invention uses a portion of the lambdoid phage tail protein as a means for linking gene-product and gene during the assembly stage of lambdoid phage replication.

That is, during lambdoid phage replication, tail proteins assemble into a matrix which forms the tubular tail. The tubular tail is attached to a head which encapsulates the phage genome. It has now been discovered that (1) phage assembly is not disrupted when recombinant lambdoid phage tail proteins are present, (2) recombinant lambdoid phage tail proteins can be integrated into the assembling matrix, and (3) integration into the matrix can be directed to occur in a surface-accessible orientation.

The present invention can be advantageously applied to the production of biologically active multimeric polypeptides of predetermined activity, i.e., it can be used to produce enzymes, lectins, ligands, receptors, and the like that have a preselected activity.

Thus, the present invention provides for linking the functions of biologically active monomeric or multimeric polypeptides and lambdoid phage replication in a method for isolating a biologically active multimeric polypeptide and the gene that encodes the polypeptide. The method produces a lambdoid phage comprised of a matrix of tail-encoded proteins that form a tubular tail attached to a matrix of head-encoded proteins that form an icosahedral head. The recombinant genome, encapsulated within the matrix of head-encoded proteins, contains genes encoding the biologically active multimeric polypeptide. The biologically active multimeric protein is surface-integrated into the encapsulating matrix via a portion of the lambdoid tail protein that is fused by a peptide bond during translation to a monomer of the multimeric polypeptide. The multimeric polypeptides and the genes which encode the polypeptides are thus physically linked during the assembly stage of the phage replication cycle. Specific biological activity of the enzyme- or lectin-coated phage advantageously provides a means for isolating a recombinant genome that encodes a desired multimeric polypeptide.

Thus in one embodiment, the invention describes a recombinant lambdoid bacteriophage vector comprising a nucleotide sequence that (i) defines the lambdoid elements for replication and packaging of the vector into an assembled bacteriophage, and (ii) encodes a conditionally suppressible cistron for expression of a tail protein and a fusion protein that comprises:

a) a promoter for transcribing the cistron, b) a first upstream translatable sequence that encodes a lambdoid bacteriophage tail polypeptide, c) a first ribosome binding site to initiate translation of the upstream translatable sequence, d) a second translatable sequence operatively linked downstream to the first translatable sequence that (i) encodes a linker polypeptide in frame with the tail polypeptide and (ii) includes a sequence adapted for ligation of an insert polynucleotide that defines a third translatable sequence downstream from the second translatable sequence that encodes a preselected polypeptide, and e) a suppressor termination codon within the second translatable sequence that upon suppression results in read-through to form a fusion polypeptide consisting of the tail polypeptide, linker polypeptide and preselected polypeptide.

The vector can optionally further include a nucleotide sequence that defines a second ribosome binding site to initiate translation of the third translatable sequence, thereby allowing the vector to also express the preselected polypeptide as a free protein.

The invention further describes a recombinant lambdoid bacteriophage particle comprising a matrix of proteins encapsulating a lambdoid genome encoding a fusion protein, wherein the matrix includes the fusion protein surface accessible in the matrix, and the fusion protein consists essentially of, in the direction of amino terminus to carboxy terminus, a lambdoid bacteriophage tail polypeptide, a linker polypeptide and a preselected polypeptide. In preferred embodiments, the genome in the bacteriophage further encodes a heterologous protein capable of forming a multimeric protein complex with the fusion protein in said matrix.

The invention further describes a fusion protein having an amino acid residue sequence that comprises, in the direction of amino terminus to carboxy terminus, a lambdoid bacteriophage tail polypeptide, a linker polypeptide and a preselected polypeptide defining a biological activity.

Libraries of recombinant lambdoid bacteriophage particles are also described wherein each particle contains a recombinant lambdoid bacteriophage vector as described hereinabove.

The invention describes a method producing a recombinant lambdoid bacteriophage of this invention, comprising the steps of:
  a) infecting an *E. coli* host strain having a termination codon suppression phenotype with a recombinant lambdoid bacteriophage vector described above; and
  b) culturing the infected host strain under bacteriophage growth conditions to produce the recombinant lambdoid bacteriophage. Preferably, the host strain is a suppressor strain selected from the group consisting of EQ166, CA168 and MC8.

Also described is a method for detecting the presence of a preselected target in a sample comprising the steps of:
  a) admixing a sample containing the preselected target with a recombinant lambdoid bacteriophage described above, wherein the preselected polypeptide defines a biologically active ligand or receptor able to bind the preselected target, under binding conditions sufficient for the target-binding bacteriophage to bind the target and form a target-ligand or receptor complex;
  b) detecting the presence of the complex, and thereby the presence of the preselected target.

Other embodiments are apparent from the detailed disclosures that follow.

BRIEF DESCRIPTION OF THE DRAWINGS

In the drawings forming a portion of this disclosure:

FIG. 2 illustrates partial sequence of the λblue and λfoo vectors. The partial sequences illustrate the amino acid and nucleotide sequence between the amber stop codon of the pV protein, indicated by TAG and underlined, and the downstream restriction sites. The names of the restriction sites are indicated below the sites and the nucleotide sequences defining the restriction sites are underlined. The corresponding amino acid sequence is given above the nucleotide sequence for each of λV'mcs, λblue and λfoo. The λV'mcs amino acid and nucleotide sequences are given as SEQ ID NO: 12 and SEQ ID NO: 13, respectively. The λblue amino acid and nucleotide sequences are given as SEQ ID NO: 14 and SEQ ID NO: 15, respectively. The λfoo amino acid and nucleotide sequences are given from amino acid residues 178 to 237 of SEQ ID NO 6 and base number 547 to 726 of SEQ ID NO 5, respectively. The amino acid sequence downstream of the suppressor codon is expressed at the carboxy terminus of pV in the presence of a suppressor tRNA as described in Example 1a2. Numbers in the right-hand column, from top to bottom, indicate the amino acid position from the start codon of the pV gene and the nucleotide sequence of the λ vector, from the beginning of the left arm, at the end of the respective lines.

The ProThr linker sequence in the λfoo vector (from base number 562 to 624 and amino acid residue sequence from 183 to 203 of SEQ ID NO 5) is directly downstream of the SfiI restriction site. The DNA expression control sequences for expressing translatable DNA inserted into any of the downstream restriction sites are included in the linker sequence. The Pribnow box, CAGGAA, is double underlined and is 6 nucleotides upstream of the start codon, methionine (M). The second amino acid, threonine (T), is underlined.

Figure 3:
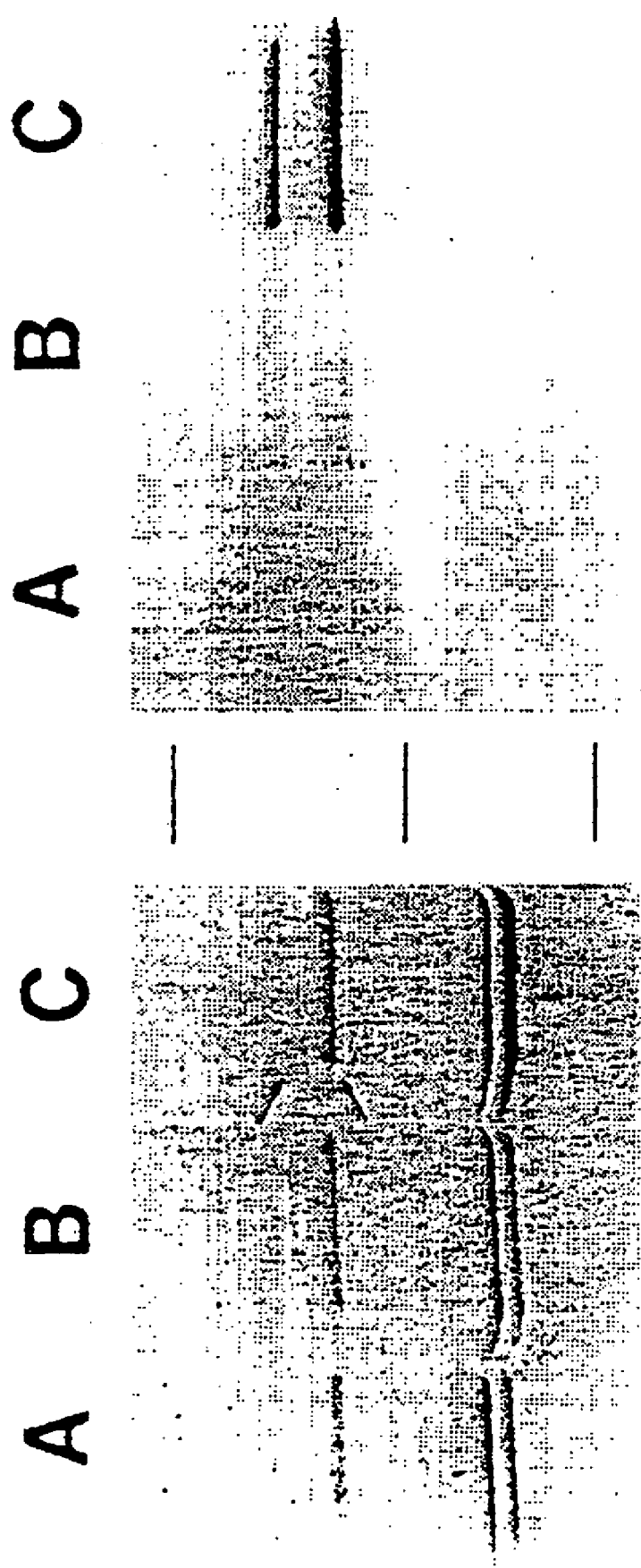

FIG. 3 illustrates the detection of λ phage proteins by gel electrophoresis and Western blotting. Purified phage proteins were detected on a polyacrylamide gel by staining with PAGE blue 84 (BDH) (lanes A, B, and C on the left side) and by reactivity with a mouse anti-β-gal antibody (lanes A, B, and C on the right side) as described in Example 2a4. Lane A is λfoo phage proteins when grown on MC8 (su$^+$); lane B is λB-gal phage proteins when grown on EQ166 (su$^-$); and lane C is λB-gal phage proteins when grown on MC8 (su$^+$). Molecular weight standards (GIBCO/BRL) (unlabeled lane in the center) are myosin heavy chain (200 kDa), phosphorylase b (97.4 kDa), and bovine serum albumin (68 kDa).

DETAILED DESCRIPTION OF THE INVENTION

A. Definitions

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552-59 (1969) and adopted at 37 CFR §1.822(b)(2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as NH$_2$ or acetyl or to a carboxy-terminal group such as COOH.

Recombinant DNA (rDNA) molecule: A DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: A rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow cloning of cDNA (complementary DNA) from mRNAs produced using reverse transcriptase.

Fusion Polypeptide: A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Cistron: Sequence of nucleotides in a DNA molecule coding for an amino acid residue sequence and including upstream and downstream DNA expression control elements.

Tricistron: Sequence of nucleotides in a DNA molecule coding for three amino acid residue sequences and including upstream and downstream DNA expression control elements.

Reading Frame: Particular sequence of contiguous nucleotide triplets (codons) employed in translation. The reading frame depends on the location of the translation initiation codon.

Suppressor Sensitive Mutations: Conditionally lethal mutations including suppressor sensitive (sus) mutations, also known as nonsense mutations. The mutational events leading to sus generate any of three nonsense codons: UAG for the amber mutations, UAA for the ochre mutations, and UGA for the opal mutations.

Suppressor Strains: Bacterial host strains generally used when working with sus mutations are a nonpermissive strain that does not allow the expression of the sus mutation (su$^-$) and a permissive or suppressor strain that does allow the expression of the sus mutation (su$^+$). These suppressor strains usually contain a mutation in a tRNA gene so that a new species of tRNA is produced which is able to give sense to an otherwise nonsense codon. In other words, to insert an amino acid at what would otherwise be a protein chain termination codon.

Homomeric: A complex comprised of at least one or more identical polypeptides.

Heteromeric: A complex comprised of at least two or more non-identical polypeptide.

Monomeric: A protein comprised of a single polypeptide.

Dimeric: A complex comprised of two identical or non-identical polypeptides.

Tetrameric: A complex comprised of four identical or non-identical polypeptides.

Multimer: A complex comprised of at least two or more polypeptides. The multimer may be homomeric or heteromeric. The multimer may be dimeric or tetrameric. The multimer may thus comprise homomeric, homodimeric, homotetrameric, heterodimeric, or heterotetrameric polypeptides.

Cis: Cis refers to when the phage genome contains a second cistron for the expression of heterosubunits, (1) other than the fusion protein subunit or (2) supplementing the amounts of fusion protein subunit; and for supplemental expression of the homomeric subunit in soluble form.

Trans: Trans refers to when the an independent genome contains a second cistron for the expression of heterosubunits, (1) other than the fusion protein subunit or (2) supplementing the amounts of fusion protein subunit; and for supplemental expression of the homomeric subunit in soluble form. The independent genomes comprise episome, plasmid, or helper phage genomes, or the second cistron may be integrated into the host genome.

B. Lambda Bacteriophage Displaying Fusion Proteins

The present invention contemplates a lambdoid bacteriophage (phage) comprising a matrix of proteins encapsulating a genome encoding a fusion protein capable of forming a/biologically active multimeric polypeptide. The phage further contains a biologically active multimeric protein comprised of monomeric polypeptides surface-integrated into the matrix via a portion of a lambdoid phage tail protein fused to at least one monomer of the biologically active multimeric protein. The biologically active multimeric protein has the capacity to have catalytic activity and therefor is referred to as an enzymatically active complex or enzyme. Alternatively, the biologically active multimeric protein has the capacity to bind a ligand or a receptor and therefor can be referred to as alternatively as a ligand-binding complex or receptor, or a ligand.

The biologically active multimeric protein in a preferred embodiment is an enzymatically active complex. That is, a complex of polypeptides capable of enzymatic activity. For example, the polypeptides are β-gal monomeric polypeptides.

Alternatively, the biologically active multimeric protein in a preferred embodiment is a ligand-binding complex. That is, a complex of polypeptides capable of binding a ligand. For example, the polypeptides are BPA monomeric polypeptides.

The polypeptides are capable of autogenous assembly into an biologically active complex, which is then expressed on the outer surface of the lambdoid phage particle in a manner accessible to substrate, i.e., they are surface-integrated into the phage. Thus, a biologically active complex is typically present on the surface of a phage of this invention. Typically, the biologically active complex is comprised of (i) a fusion polypeptide which comprises in the direction of amino terminus to carboxy terminus, a lambdoid bacteriophage tail (matrix anchor) polypeptide, a linker polypeptide, and a preselected polypeptide defining a subunit of the biologically active complex; and (ii) one or more wild-type monomeric polypeptides of the biologically active complex. Preferred are phage having a portion of the pV tail matrix anchor domain fused to a monomeric polypeptide of the multimeric complex as described further herein.

Alternatively, the polypeptides are capable of autogenous assembly into a multimeric complex, which is then expressed on the outer surface of the lambdoid phage particle in a manner accessible to ligand, for example in the case of a ligand-binding complex, they are surface-integrated into the phage. Thus, a multimeric complex of this invention is present on the surface of a phage of this invention. Typically, the ligand-binding complex is comprised of (i) a fusion polypeptide which comprises a lambdoid phage tail matrix anchor, a linker polypeptide, and a monomer of the ligand-binding complex; and (ii) one or more wild-type monomers of the ligand-binding complex.

Because the enzymatically active complex is linked to the phage in a surface accessible manner, the phage can be advantageously used as a solid-phase catalyst. In preferred embodiments, the phage are linked, preferably removably linked, to a solid (aqueous insoluble) matrix such as agarose, cellulose, synthetic reins, polysaccharides and the like. For example, the phage can be applied to and retained in a column and maintained under conditions that support retention of the phage. An aqueous composition containing a substrate that is catalyzed by the enzymatically active complex expressed by the phage is then passed through the column at a predetermined rate and under substrate-enzyme binding conditions to form a solid-phase substrate-enzyme complex. The column is then maintained under conditions favorable for the catalytic conversion of substrate to product or products. The product or products can then be removed and recovered by washing the column with a buffer that promotes elution of the product or products.

Alternatively, purified phage can be admixed with a aqueous solution containing the substrate to be catalyzed. The enzyme/substrate binding reaction admixture thus formed is maintained for a time period and under binding conditions sufficient for a phage-linked enzyme-substrate complex to form and under catalytic conditions sufficient for catalysis to occur. The phage-bound enzyme (enzyme-bearing phage) are then separated and recovered from the product or products, such as by centrifugation, electrophoresis, precipitation, and the like.

Alternatively, because the ligand-binding complex or receptor is linked to the phage in a surface accessible manner, the phage can be advantageously used as a solid-phase affinity sorbent. In preferred embodiments, the phage are linked, preferably removably linked, to a solid (aqueous insoluble) matrix such as agarose, cellulose, synthetic reins, polysaccharides and the like. For example, the phage can be applied to and retained in a column and maintained under conditions that support retention of the phage. An aqueous composition containing a ligand that binds to the receptor expressed by the phage is then passed through the column at a predetermined rate and under ligand-binding conditions to form a solid-phase receptor-ligand complex. The column is then washed to remove unbound material, leaving the ligand bound to the solid-phase phage. The ligand can then be removed and recovered by washing the column with a buffer that promotes dissociation of the receptor-ligand complex.

Alternatively, purified phage can be admixed with a aqueous solution containing the ligand to be affinity purified. The receptor/ligand binding reaction admixture thus formed is maintained for a time period and under binding conditions sufficient for a phage-linked receptor-ligand complex to form. The phage-bound ligand (ligand-bearing phage) are then separated and recovered from the unbound materials, such as by centrifugation, electrophoresis, precipitation, and the like.

Phage of this invention can be labeled when used in a diagnostic method of this invention. Preferred labels include radioactively labeled nucleic acids incorporated into the phage genome, or radioactively labeled amino acids incorporated into protein components of the phage particle. Preparation of labeled phage can be routinely prepared by growing phage as described herein, but including radiolabeled nucleotides or radiolabeled amino acids in the culture medium for incorporation into nucleic acids or polypeptides of the phage, respectively. Exemplary labels are $^3$H-thymidine or $^{35}$S-methionine. Other isotopic labels and other nucleotide or amino acid precursors are readily available to one skilled in the art. The labeled phage preferably contains sufficient label to be detectable in a binding assay of this invention, i.e., the phage is detectably labeled.

1. Lambdoid Bacteriophage Classification and Structure

Lambdoid bacteriophages are a group of related viruses that infect bacteria. They are termed lambdoid, or "lambda-like", because the first member to be described was lambda (λ). The lambdoid bacteriophage (phage) are members of a group which have three common properties: the ability to recombine when intercrossed, DNA molecules possessing identical pairs of cohesive ends, and prophages that are inducible by ultraviolet irradiation. The best known members of the lambdoid group comprise λ, 21, Ø80, Ø81, 82, 424, and 434.

2. Fusion Display Protein

Lambdoid phage particles are about half protein and half DNA. The mature capsule of lambdoid phage is comprised of a morphologically distinct head and tail. Each phage particle contains one double-stranded DNA molecule capable of replication that is encapsulated in an icosahedral head from which projects a tubular tail.

The bacteriophage head and tail are assembled separately and then together to form a phage particle capable of infecting and replicating in a suitable host. The bacteriophage head encapsulates the phage genome. The steps of bacteriophage λ head and tail morphogenesis are complex and proceed in an obligate order. Details of head and tail morphogenesis are described fully in: "Lambda II", R. W. Hendrix, J. W. Roberts, F. W. Stahl, and R. A. Weisberg, eds. Cold Spring Harbor Laboratory, Cold Spring Harbor, N.Y., pp. 279-304 and 331-363 (1983), respectively.

The finished lambdoid head contains amino acid residue sequences encoded by six of the twelve genes required for its assembly. The assembled lambdoid head thus contains gene products of six genes (W, B, C, D, E, and FII) and eight types of polypeptides (pE, pD, pB, pW, pFII, pB* [pB* refers to a cleavage product of pB], pXI, and pX2). The mature head of λ phage contains 420 molecules of each of two major proteins, the amino acid sequences encoded by pD and pE (Imber et al., *J. Mol. Biol.*, 139:277, 1980). The mature head forms an icosahedral shape. The inner portion of the icosahedral head is a shell composed of only pE. pD occupies parts of the valleys on the surface of the pE shell (Georgopoulous et al., *J. Mol. Biol.*, 76:45, 1983). The remaining proteins are a part of the proximal vertex, or "head-tail" connector, located at the 12 vertices of the head. Thus, eight types polypeptides are assembled on the surface of the lambda head and provide the means for display of a foreign polypeptide in a surface-accessible manner on the surface of the lambdoid phage particle.

Twelve tail genes have been reported: Z, U, V, G, T, H, "208", M, L, K, I, and J (Campbell, et al., *Virology*, 14:22, 1961; Thomas et al., *Mutat. Res.*, 4:735, 1967; Mount et al., *Virology*, 35:134, 1968; Parkinson, *Genetics*, 59:311, 1968). Most of the tail gene products are found in assembled phage particles.

The lambdoid phage tail is a thin flexible tube, ending in a small conical part, and a single tail fiber (Kellenberger et al., in: "*The bacteriophage lambda*", A. D. Hershey, ed., Cold Spring Harbor Laboratory, Cold Spring Harbor, N.Y., p. 271, 1971; Hohn et al., *Curr. Top. Microbiol. Immunol.*, 78:69, 1977). Both the conical part and the tail tube have cross striations in electron micrographs and consist of 3 or 4 disks and 32 disks, respectively. The tail tube can be dissociated into ring-like structures by chemical treatments. Each ring-like structure corresponds to single- or multi-layered disks (Bleviss et al., *Can. J. Microbiol.*, 17:947, 1971; Katsura et al., *J. Supramol. Struct.*, 2:239, 1974). An end view shows that there are probably six small knobs arranged around the core. The disk is composed of six subunits of pV (Buchwald et al., *Virology*, 42:390, 1970; Casjens et al., *J. Mol. Biol.*, 88:535, 1974), each subunit of pV consisting of two separate folding domains.

Most of the tail-gene products are found in finished phage particles and their locations in the structure are known with varying degrees of certainty. pJ is the part of the tail that interacts directly with the surface of the host cell, as judged by serological (Dove, *J. Mol. Biol.*, 19:187, 1966; Buchwald et al., *Virology*, 38:1, 1969) and genetic (Mount et al., *Virology*, 35:134, 1968) evidence. Thus, the pJ is thought to be the tail fiber. The major tail protein, pV, forms the tail tube which comprises a stack of 32 hexameric rings (Casjens et al., *J. Mol. Biol.*, 90:20, 1974; Katsura et al., *Virology* 76:129, 1977). A hexamer of pU is attached to the head-proximal end of the tail tube and connects the tail to the head. pU and pZ are believed to be inside the tubular tail. pG, pM, pL, and pT are a part of the tail tip which forms the conical portion plus the tail fiber. Thus, pJ, pV, pG, pM, and pT are assembled on the surface of the lambda tail and provide a preferred means for display of a foreign polypeptide in a surface-accessible manner on the surface of the lambdoid phage particle.

The matrix anchor domain of a lambdoid phage tail protein is the amino terminal region of the tail protein and is also known as the core domain. The core domain and the protruding domain of the pV polypeptide seem to be folded into more or less independent domains. Of the two domains, the core domain is responsible for the maintenance of the total shape of the tail and for the injection of phage DNA into the host cell. Therefore, the core domain is responsible for the assembly and function of the infectious phage particles (Katsura, *J. Mol. Biol.*, 146:493-512, 1981). Preferred tail proteins are found in the tail proteins encoded by pV. Mutants of pV have been isolated in which as much as one third of the pV molecule is absent from the carboxy terminal end, yet the tails function normally. In these mutants, the domain of pV that constitutes the outer knob is missing (Katsura, *J. Mol. Biol.*, 146:493-512, 1981).

The amino acid residue sequence of a preferred matrix anchor domain is derived from the λ phage gene V tail protein (also designated pV) and has an amino acid residue sequence shown in SEQ ID NO 1 from residue 1 to residue 246. Exemplary matrix anchors would consist of at least residues 1 to 177, or residues 1 to 230 of pV. Gene V tail protein is present on a mature phage along the phage tail with typically about 180 to 200 copies of the tail protein.

A phage particle of this invention contains at least one fusion protein of this invention on the surface of the phage particle. The actual amount of fusion protein present on the surface of a phage particle depends, in part, on the choice of protein matrix anchor present in the fusion protein. Where the anchor is derived from pD, there is the potential for hundreds of fusion proteins depending on growth conditions and other factors. Where the anchor is derived from the more preferred pV, there are typically 1 to 4 fusion proteins on the particle surface depending on the growth conditions and other factors as discussed herein. Preferably, a phage particle contains from about 1 to about 4 pV-derived fusion proteins on the surface of each particle, and more preferably about 1 to 2 fusion proteins per particle. Exemplary amounts of surface fusion protein are shown by the electron micrographs described in Example 2a6) that describe particles having about 1 to 3 pV-derived fusion proteins per particle. The remaining pV tail proteins are either wild-type pV tail proteins or the pV amino terminal domain tail proteins.

The assembly of the λ tail during phage morphogenesis is regulated by variation in the relative amount of each tail protein synthesized, the timing of the production of each tail protein, and the regulation of protein polymerization both by initiation and by termination.

For further detailed descriptions of the structure of lambdoid phage particles, their coat and tail proteins and particle assembly, see Georgopoulos, et al. and Katsura, in: "Lambda II", R. W. Hendrix, J. W. Roberts, F. W. Stahl, and R. A. Weisberg, eds. Cold Spring Harbor Laboratory, Cold Spring Harbor, N.Y., pp. 279-304 and 331-363, 1983, respectively.

a. Phage Display Proteins

The protein matrix anchor provides a means for display of a foreign protein on the surface of the phage particle of this invention in a surface accessible manner. The protein matrix anchor may be selected from the group consisting of any of the proteins displayed on the surface of the phage particle and comprise the head proteins pE, pD, pB, pW, pFII, pB [pB* refers to a cleavage product of pB], pXI, and pX2 and the tail proteins pJ, V, G, M, and T.

The gene product of pV is the major tail protein and forms the tail tube (Buchwald et al., *Virology*, 42:390, 1970) as described herein above. The gene product of pV is present on the surface of the phage tail at about 192 copies. pV contains 246 amino acid residues (SEQ ID NO 1).

A member of the lambdoid phage, phage lambda, has been described having a mutation in the pV in which as much as one third of the pV protein is absent from the carboxyterminal end, yet the tails appear to function normally. The domain of pV that constitutes the outer knob is missing in these mutants (Katsura, *J. Mol. Biol.*, 146:493-512, 1981). The mutant, or truncated, pV comprises a protein that is from about amino acid residue sequence 1 to 176 (SEQ ID NO 1 from positions 1 to 176). In preferred embodiments, the pV polypeptides will generally have fewer than 240 amino acid residues, more usually fewer than about 230 amino acid residues, while normally having greater than 150 amino acid residues, usually greater than about 170 amino acid residues, more usually greater than about 180 amino acid residues. Preferably, the pV will be from about 185 to about 220 amino acid residues in length. pV polypeptides of sufficient length to form a core domain capable of assembling and forming infectious phage particles are preferred. pV polypeptides of sufficient length and/or structure to display the fusion protein, which has been incorporated into the phage tail matrix, in a surface accessible manner are also preferred.

The truncated pV proteins in the mutant λ described herein were synthesized and assembled onto phage particles in amounts of about 192 copies per particle, a density at which wild-type pV is usually found.

The ratio of wild-type to truncated pV protein, truncated pV protein to fusion protein, and wild-type pV protein incorporated into the phage tail matrix may be critical to the formation of functional (i.e., infectious) phage particles. This ratio can be varied by several means for expressing the polypeptides by the use of transcriptional and translational regulators, varying the copy number of the genes, and the like as well known by those of skill in the art.

Preferred ratios of fusion protein to truncated pV protein are those which result in the formation of functional phage particles. Preferred ratios of fusion protein to truncated pV protein are about 1 to 10 fusion proteins to 200 truncated pV protein, more preferred ratios are about 1 to 5 to 200, and most preferred ratios are about 1 to 192.

b. Displayed Proteins/Epitopes

A fusion protein in a bacteriophage of this invention typically displays a preselected polypeptide which defines a cytoplasmic protein or a biologically active portion of the cytoplasmic protein. Cytoplasmic proteins are those proteins which fold and assemble in the cytoplasm. Cytoplasmic proteins carry out a particular function which may be structural, enzymatic, or regulatory. Due to the broad applicability of the invention, the species of cytoplasmic protein to be displayed need not be limited. Preferred biological activities include enzymes, ligands, receptors, co-factors, structural proteins, and the like.

The replication and assembly of lambdoid phage occurs in the cytoplasm, therefore, a fusion protein consisting of a phage tail polypeptide and a cytoplasmic protein would be assembled into the lambdoid phage matrix in the cytoplasm and does not require that the fusion protein be secreted prior to assembly.

The displayed polypeptide of this invention may be the complete naturally-occurring polypeptide or a portion of the naturally-occurring polypeptide. If a portion of the polypeptide is displayed, the portion that confers the desired biological activity or function would be displayed. The portion of the polypeptide may define a structural or functional domain.

The displayed polypeptide of this invention may be a monomeric or multimeric protein, that is, the displayed polypeptide may comprise one or more subunits. The displayed multimeric protein can be homomeric or heteromeric, that is, the displayed multimeric protein may comprise more than one identical or nonidentical subunits.

An exemplary enzymatic displayed polypeptide of this invention is β-galactosidase (β-gal). β-gal is a tetramer of four identical monomers and is therefore a homotetramer. The tetramer of β-gal has a molecular mass of 465 kDa. β-galactosidase activity is associated with the tetrameric structure. β-galactosidase activity is not associated with either dimer or monomers of β-gal. The gene for β-gal has been cloned and sequenced, and is well known and readily available to the public. The sequence has been published, and is also available on public databases such as GenBank. β-gal cleaves a β-galactoside into its component sugars and is most commonly used to cleave lactose to form glucose and galactose. β-gal has been well characterized and further descriptions and details can be found in: "*The Operon*", J. H. Miller and W. S. Reznikoff, eds., Cold Spring Harbor Laboratory, pp. 89-121 (1980). It is also widely used commercially due to its ability to function as a sensitive indicator in recombinant DNA vectors. The nucleotide sequence encoding a monomer of β-gal was inserted into the DNA expression vector of this invention and is described in Example 2. The first amino acid residue of the β-gal monomer is the most preferred site of fusion to the pV protein, however, other sites of fusion may also be used, so long as the fusion protein has enzymatic activity.

Another exemplary displayed polypeptide of this invention is *Bauhinia purpurea* lectin (BPA). BPA is a tetramer of four identical subunits and is therefore a homotetramer. The tetramer of BPA has a molecular mass of 120 kDa. BPA has a low association constant of $10^5$ $M^{-1}$ with mucin (Osawa et al., *Ann. Rev. Biochem.*, 56:21-42, 1987).

BPA is a plant lectin that can be purified from *B. purpurea* seeds (Irimura et al., *Arch. Biochem. Biophys.*, 151:475-482, 1972). Lectins are proteins with carbohydrate-binding sites which have the ability to agglutinate erythrocytes. BPA exhibits a high degree of specificity for N-acetylgalactosamine and galactose and has been shown to bind specifically to β-D-galactose residues, especially to Galβ1-3-N-acetylgalactosamine. Lactose and galactose have been shown to competitively inhibit binding of BPA to mucin while maltose and glucose have not.

The cDNA for EPA was recently isolated from a cDNA library of germinated *B. purpurea* seeds (Kusui et al., *J. Biochem.*, 109:899-903, 1991). The cloned BPA cDNA comprised 1,152 nucleotides and the open reading frame of the cDNA encodes a polypeptide of 290 amino acid residues including a signal peptide composed of 28 amino acid residues. The cDNA containing amino acid residue sequences encoding the mature lectin protein without the signal peptide was inserted into the DNA expression vector of this invention as described in Example 3. The first amino acid residue of the mature BPA monomer without the signal peptide is the most preferred site of fusion to the pV protein, however, other fusion sites may also be so long as the fusion protein has lectin binding activity.

c. Linker Polypeptides

The invention uses a linker polypeptide as a means for linking the upstream and downstream polypeptides, i.e., the phage matrix anchor (tail) and the displayed (biologically active) polypeptides. The linker polypeptide provides a polypeptide which facilitates the independent folding and spatial separation of the upstream and downstream polypeptides. In addition, the invention uses a linker polypeptide as a means for the physical separation of the upstream and downstream polypeptides. The linker polypeptide can optionally provide a proteolytic cleavage site capable of being cleaved by a protease and thereby allowing a means for physically separating the upstream and downstream polypeptides. The protease cleaves the peptide bonds at a specific site in the linker polypeptide hereby eliminating the physical linkage of the upstream and downstream polypeptides. Thus, cleavage of the linker polypeptide at a specific site provides a means for the physical separation of the upstream and downstream polypeptides.

The linker peptide of the present invention preferably consists of amino acid residue sequence of sufficient length or size to confer a spatial separation between the upstream and downstream polypeptides and allow efficient incorporation of the upstream and downstream polypeptides into the lambdoid phage tail matrix. The linker peptide is typically about 10 to 100 amino acid residues in length. Preferably, the linker peptide is 15 to 50 amino acid residues. More preferably, the linker peptide is 20 to 40 amino acid residues. An exemplary linker having 36 amino acid residues is described in the Examples and has a sequence from amino acid residues 178 to 213 of SEQ ID NO 6.

In addition, the amino acid residue sequence of the linker polypeptide confers a flexibility upon the linker polypeptide. The flexibility contributes to the independent folding and spatial separation of the upstream and downstream polypeptides and efficient incorporation of the upstream and downstream polypeptides into the lambdoid phage tail matrix. The flexibility conferred by the linker polypeptide is an inherent property of the amino acid residue sequence comprising the linker polypeptide.

Preferably, the linker polypeptide consists of an amino acid residue sequence that is selected from the group comprising the hinge region of an immunoglobulin molecule, the Pro-Thr sequence of *C. fimi* endoglucanase and exoglucanase, and alternating Pro-Ser amino acid residues. Most preferably, the linker polypeptide of the present invention consists of alternating prolyl and theonyl amino acid sequence residues. Such alternating prolyl and theonyl amino acid sequence residues can be found in the Pro-Thr sequence of *Cellulomonas fimi* endo-β-1,4-glucanase (Wong, et al., *Gene*, 44:315-324, 1986). In the endo-β-1,4-glucanase molecule, the Pro-Thr amino acid residue sequence links two domains, the cellulose-binding domain and catalytic domain, in *C. fimi* exoglucanase (Cex) and endoglucanase (CenA), and is similar in structure to the hinge-region of IgA$_1$ immunoglobulins (Ong et al., *Biotechnology*, 7:604-607, 1989). The linker polypeptide thus provides a means for the spatial separation of the upstream polypeptide from the downstream polypeptide, the individual folding of the upstream and downstream polypeptides, and efficient incorporation of the fusion polypeptide into the lambdoid phage tail matrix.

The linker polypeptide, Pro-Thr amino acid sequence residue, also provides a means for the physical separation of the upstream and downstream polypeptides by cleavage of the peptide bond at a specific site by a protease. Preferable proteases for use in this invention include *C. fimi* protease (Gilkes et al., *J. Biol. Chem.*, 263:10401-10407, 1988) and collagenase.

C. Infectious Phase Particle Structure

A lambdoid phage particle of this invention is produced by standard lambdoid phage particle preparation methods and depends on the presence in a DNA expression vector of this invention of a lambdoid phage tail protein pV as described herein to provide the polypeptides necessary for (1) production of an assembled lambdoid phage tail and (2) the ability of the assembled lambdoid phage tail to bind to and infect suitable host cells. Such phage tail proteins can be assembled to form an infectious phage particle when present in a bacterial cell host upon introduction of genetic complementation to provide the phage tail proteins required for production of infectious phage particles. Such tail proteins can be supplied either in cis or in trans from in vivo or in vitro sources (see for example, Katsura, in: "Lambda II", R. W. Hendrix, J. W. Roberts, F. W. Stahl, and R. A. Weisberg, eds. Cold Spring Harbor Laboratory, Cold Spring Harbor, N.Y., pp. 279-304, 1983.

A typical and preferred method for genetic complementation is to infect a bacterial host cell containing a DNA expression vector of this invention with a helper lambdoid phage, plasmid, or phagemid thereby providing the genetic elements required for phage particle assembly. Genetic complementation would thus provide the ratio of fusion protein to tail protein required to form a functional lambdoid tail protein as described herein. Alternatively, genetic complementation can provide the fusion protein of this invention to be incorporated into the phage tail matrix to form a functional phage tail protein which displays the multimeric complex in a surface accessible manner.

Lambda phage which have a mutation in the pV have been described in which as much as one third of the pV molecule is absent from the carboxy terminal end as described herein. These lambda phage tails assemble and function normally. The truncated pV proteins were synthesized and assembled onto phage particles in amounts of about 192 copies per particle, a density at which wild-type pV is usually found. These expressed truncated pV proteins, which include the amino acid residue sequences from about 1 to 176, do not suggest that a combination of wild-type and truncated pV proteins can be assembled to form a functional phage particle. The ratio of wild-type and truncated pV proteins required for the formation of functional phage particles are also described herein. It is therefore unexpected that a functional phage particle can be assembled with a combination of wild-type and truncated pV proteins or a combination of truncated pV and fusion proteins.

D. Bacteriophage Genome

The genome of the lambdoid bacteriophage contains all the elements necessary for replication, packaging of the genome, a minimum number of proteins able to assemble into an infectious phage particle. The genome of a lambdoid bacteriophage may be divided into three regions. The left-hand region includes all of the genes (from A to J) whose products are necessary to package phage DNA and produce an infectious phage particle. The central region (between genes J and N) does not contain genes whose products are necessary for the production of infectious phage particles. The remaining portion of the genome, from N rightward, includes all the major control elements, the genes necessary for phage replication (O and P), and those for cell lysis (S and R). The lambdoid phage replication pathway produces a linear polymer of the lambdoid bacteriophage genome which can be replicated and packaged into a λ head. The λ head and tail assemble to form an infectious phage particle capable of infecting and replicating in a suitable host.

In addition the bacteriophage genome of this invention encodes a cistron that expresses the biologically active multimeric complex of this invention in a surface accessible manner on the surface of phage particles. The cistron is adapted for the insertion of insert DNA and is described further herein. The expression of the biologically active multimeric complex is under a type of translational control known as conditional suppression and is further described herein. Conditional suppression requires the use of a suppressor codon, such as TAG, and the use of suppressor and nonsuppressor hosts. Expression of the bacteriophage genes required for replication, packaging, and the like are not effected by the use of suppressor and nonsuppressor hosts.

E. Polyvalent Phase Having Different Display Proteins

The invention also contemplates lambdoid bacteriophage particles having multiple species (polyvalent) of fusion proteins of this invention, thereby providing polyvalent phage particles. A phage particle having multiple displayed biological activities provides the advantages of polyvalence, crosslinking, labeling and the like well characterized properties, the specifics of which depend upon the particular fusion proteins and associated biological activities being displayed.

For example, a bivalent phage may contain a first fusion protein that provides a binding activity of interest useful for detection of a receptor, and the second fusion protein provides a detection means, such as a catalytic activity. Thus, the phage serves to conjugate two separate biological activities, namely a tag and a binding activity. Alternatively, one can use a bivalent (or multivalent) phage as a crosslinker for coupling two functions, such as ligands for two different receptors. Other permutations will be apparent to one skilled in the art.

The presentation of two or more different fusion proteins on a phage of this invention can be accomplished by a variety of formats, and therefore need not be limiting. For example, one can introduce two separate biological activities onto two fusion proteins which have the same lambdoid matrix anchor, or have different anchors.

In the case of using the same anchor, for example pV, a first pV fusion protein is expressed by a first cistron, and a second pV fusion protein is expressed by a second cistron. There is no particular limitation on the location of the first and second (or third, etc., if more) cistrons, and can be positioned on the same vector and under the control of the same or different promoters, or can be positioned on separate vectors, for example one on a plasmid and the other on the lambdoid vector.

In the case of using different anchors, for example pV and pD, a pV fusion protein is expressed by a first cistron, and a pD fusion protein is expressed by a second cistron, with the cistron configurations varying as discussed above.

In another permutation on this theme, one can utilize the differences between libraries based on pV- and pD-derived membrane anchors due to their inherent differences in valency. Because a library of phage having the pV-derived membrane anchor will typically contain only 1 to 4 copies of the enzyme- or ligand-binding complex on the surface of each phage particle, the phage presents a binding complex of relatively "low" valency, approaching one. In contrast, a library of phage having a pD-derived membrane anchor will typically contain 20 to 420 copies of the substrate- or ligand-binding complex on the surface of each phage particle, the particle presents a relatively "high" valency. Thus, pV-based libraries are referred to as monovalent and pD-based libraries are referred to as multivalent.

F. Polypeptides

In another embodiment, the present invention contemplates a polypeptide (fusion protein) comprising an amino-terminal lambdoid matrix anchor polypeptide domain, a linker polypeptide domain, and a preselected polypeptide domain defining a biological function.

The polypeptide is a fusion polypeptide having a preselected biological activity comprised of an amino acid residue sequence that defines the biologically active domain of a protein positioned, located at the carboxy terminus of the fusion protein. That is, the preselected (inserted) polypeptide domain in the fusion polypeptide is the biologically active domain of a protein and is also referred to as a biologically active polypeptide.

In one embodiment, a polypeptide of this invention has an amino acid residue sequence that can be represented by the formula, shown in the direction of amino- to carboxy terminus:

$$NH_2—O—U—V—COOH, \quad (F1)$$

where O represents an amino acid residue sequence defining a lambdoid matrix anchor polypeptide, U represents a linker polypeptide, and V represents an amino acid residue sequence defining a biologically active-domain such as a substrate- or ligand-binding receptor polypeptide.

In the formula (F1), the lambdoid matrix anchor polypeptide and linker polypeptide are as defined herein above. Thus, a preferred polypeptide comprises a preselected polypeptide operatively linked at its amino-terminus to the lambdoid matrix anchor polypeptide and the linker polypeptide.

In preferred embodiments the lambdoid matrix anchor polypeptide domain is derived from the lambdoid phage pV or pJ tail proteins or from the lambdoid phage pD head protein as described herein.

In preferred embodiments, the biologically active protein is a polypeptide chain of a catalytic multimeric protein. More preferably the multimeric polypeptide is an enzymatic complex.

In other preferred embodiments, the biologically active polypeptide is a polypeptide chain of a lectin protein. More preferably the multimeric protein is a mucin-binding complex.

Preferred multimeric polypeptides include enzymes, lectins, and the like.

As used herein with regard to polypeptides, the phrase "operatively linked" means that polypeptide fragments, or protein domains represented by polypeptides, have been covalently joined into a single polypeptide polymer, preferably by conventional amide bonds between the adjacent amino acids being linked in the polypeptide.

In one embodiment, V is an amino acid residue sequence that defines the catalytic domain of a multimeric molecule, and preferably is an enzymatic polypeptide. Most preferred is a polypeptide where V is a β-gal monomeric polypeptide.

In another embodiment, V is an amino acid residue sequence that defines the ligand-binding domain of a multimeric receptor molecule, and preferably is a lectin polypeptide. Most preferred is a polypeptide where V is a BPA monomeric polypeptide.

In another embodiment, U can define a linker polypeptide containing a proteolytic cleavage site, such as the sequence of amino acids found in a precursor protein, such as C. fimi exoglucanase or endoglucanase, collagen, prothrombin, factor X and the like, that defines the site of cleavage of the polypeptide. A fusion polypeptide having a cleavage site provides a means to purify the polypeptide away from the phage particle to which it is attached.

The polypeptide linker U can have any sequence of amino acid residues of from about 1 to 50 amino acid residues in length. Typically the spacer residues are present in a polypeptide to accommodate the continuous reading frame that is required when a polypeptide is produced by the methods disclosed herein using a DNA expression vector of this invention. Further, the linker polypeptide U provides a means for the spatial separation of the upstream and downstream polypeptides and provides for the independent folding of the polypeptides.

Preferably the receptor produced by the subject invention is multimeric and is therefore normally comprised of more than one identical polypeptide chain, which together assume a conformation having a binding affinity, or association constant for the preselected ligand that is different, preferably higher, than the affinity or association constant of any of the polypeptides alone or in pairs, i.e., as monomers or dimers. The multimeric receptor is referred to as a substrate- or ligand-binding multimeric receptor to connote its ability to bind substrate or ligand.

Thus, a preferred embodiment contemplates a ligand-binding multimeric receptor comprising first, second, and third polypeptides. The first polypeptide is a fusion polypeptide comprising an amino-terminal lambdoid matrix anchor domain, a linker polypeptide, and a preselected polypeptide. The second polypeptide is a lambdoid matrix anchor domain. The third polypeptide is a wild-type monomer polypeptide. A particularly preferred ligand-binding multimeric receptor contains a matrix anchor-derived from pD, pV or pJ as described herein.

A ligand-binding multimeric receptor is referred to as an epitope-binding complex to connote that the complex has a capacity to bind an epitope present on a ligand, and to connote that the multimeric receptor is formed by the association (complexation) of more than one polypeptide as described herein.

The polypeptide chains are preferably derived from the coding region of an enzyme, lectin, receptor, ligand or other protein having a desirable biological activity. Typically, polypeptides comprising the monomeric polypeptides are employed together for binding a preselected substrate or ligand.

Thus, one embodiment contemplates a substrate-binding multimeric receptor in which the polypeptides are β-gal monomeric polypeptides. An alternative embodiment contemplates a ligand-binding multimeric receptor in which the polypeptides are BPA monomeric polypeptides.

A receptor produced by the subject invention can be active in monomeric as well as multimeric forms. For example, β-gal substrate binding polypeptide produced by the present invention can be advantageously combined in the multimer to modulate the activity of the monomeric polypeptides or to produce an activity unique to the multimer. Alternatively, the BPA ligand-binding polypeptide produced by the present invention can be advantageously combined in the multimer to modulate the activity of the monomeric polypeptides or to produce an activity unique to the multimer.

G. Method for Producing Bacteriophage Particle Having a Heterologous Cytoplasmic Protein on its Surface The present invention also describes methods for producing proteins on the surface of lambda phage particles and for producing recombinant lambdoid bacteriophage particles. The methods are based generally on the use of a lambdoid expression vector which can be produced from a variety of sources of lambdoid genomes, as described herein.

The manipulation methods used to identify proteins displayed on the surface of phage particles have been extensively described in the literature, and will not be reviewed in detail herein, except for those features required to use unique embodiments of the present invention. However, the methods generally involve the use of a lambdoid phage (lambda) surface expression vector system for cloning and expressing protein species.

In one exemplary embodiment, the method involves preparing a lambda vector capable of displaying β-gal on the surface of its phage particles by using E. coli β-gal as a source of the β-gal gene. β-gal is a multimeric protein which assembles four β-gal monomers to form a tetrameric structure. The formation of the tetrameric structure is necessary for the functional activity of β-gal.

In another exemplary embodiment, the method involves preparing a lambda vector capable of displaying BPA on the surface of its phage particles by using B. purpurea cDNA as a source of the BPA gene. BPA is also a multimeric protein which assembles four BPA monomers to form a tetrameric structure. Alternatively, the displayed protein may be a monomeric protein.

The method for producing a biologically active multimeric polypeptide complexes generally involves (1) preparing a polypeptide-encoding gene and inserting the gene into a lambdoid bacteriophage vector of this invention using genomic DNA or cDNA as a source for the DNA inserts, (2) expressing the fusion protein containing the polypeptide-encoding gene in said vectors capable of expressing and assembling a multimeric polypeptide molecule on the surface of a lambdoid phage particle, and (3) alternatively (i) isolating the surface-expressed phage particle using immunoaffinity techniques such as panning of phage particles against a preselected biological binding activity, thereby isolating one or more species of phage containing particular polypeptide-encoding genes and protein molecules that have the desired biological binding activity, or (ii) isolating the surface-expressing phage particle using enzymatic techniques such as contacting the phage particle with a preselected substrate, maintaining the phage-substrate under conditions favoring catalysis, and detecting the formation of products, thereby identifying one or more species of phage containing particular polypeptide-encoding genes and protein molecules that catalyze a preselected enzymatic reaction, or (iii) isolating the surface-expressed phage particle using techniques such as panning of phage particles immunoreactive with a preselected antibody, thereby isolating one or more species of phage containing particular polypeptide-encoding genes and protein molecules that bind with the preselected antibody.

Alternatively, the surface-expressed phage particle can be isolated using immunoaffinity techniques such as immunoprecipitation of the phage particles with a preselected antibody, thereby isolating one or more species of phage containing particular polypeptide-encoding genes and protein molecules that immunoreact with the preselected antibody.

The surface-expressed phage particle can also be isolated by a functional technique such as an enzymatic reaction with a preselected substrate, thereby isolating one or more species of phage containing particular polypeptide-encoding genes and protein molecules that enzymatically react with the preselected substrate.

The surface-expressed phage particle can also be isolated by a functional technique such as a ligand-binding reaction with a preselected ligand, thereby isolating one or more species of phage containing particular polypeptide-encoding genes and protein molecules that bind to the preselected ligand.

As described herein, the resulting phage can be manipulated to increase and/or alter the specificities or affinities of the polypeptide(s) encoded in the lambdoid vector to produce and subsequently identify additional, desirable, activities of the present invention.

For example, the β-gal-encoding genes can be randomly mutagenized and subsequently screened for desirable catalytic, affinity, and specificity capabilities. Alternatively, the β-gal encoding genes can be mutagenized in a site-directed manner and subsequently screened for desirable catalytic, affinity, and specificity capabilities.

In addition, the BPA-encoding genes can be randomly mutagenized and subsequently screened for desirable affinity and specificity capabilities. Alternatively, the BPA-encoding genes can be mutagenized in a site-directed manner and subsequently screened for desirable affinity and specificity capabilities.

In one embodiment, the pV-polypeptide and polypeptide monomer genes can be inserted into separate, monocistronic expression vectors, referred to as a "binary" system. In this method, step (2) above differs in that the combining of pV-polypeptide and polypeptide monomer encoding genes occurs by the co-introduction of the two binary plasmids into a single host cell for expression and assembly of a phage having the surface accessible polypeptide multimeric molecule.

As a further characterization of the present invention the immunoreactivity of the β-gal multimeric polypeptide on the surface of lambda phage is determined. The immunoreactivity provides essential information regarding the conformation of the multimeric polypeptides.

Inhibition assays in which various sugars competitively inhibit binding of BPA to its ligand, mucin, further characterize the present invention.

Exemplary preparations of functionally active multimeric polypeptides displayed on the surface are described in the Examples. The isolation of a particular vector capable of expressing an polypeptide of interest involves the introduction of the expression vector into a host cell permissive for expression of lambdoid phage genes and the assembly of phage particles. Where the binary vector system is used, both vectors are introduced in the host cell. Typically, the host is *E. coli*. The resulting host cell is cultured to allow the introduced phage and polypeptide genes to be expressed, and for phage particles to be assembled and released from the host cell. The released phage particles are then harvested (collected) from the host cell culture media and screened for desirable immunoreaction, enzymatic, and ligand-binding properties. Typically, the harvested particles are "panned" for binding to a preselected ligand, enzymatic activity, or for immunoreaction with a preselected antibody. The strongly binding, enzymatic, or immunoreactive particles are then collected, and individual species of particles are clonally isolated and further screened for enzymatic activity, binding affinity, or immunoreactivity. Phage which produce biologically active polypeptides are selected and used as a source of enzymatic, ligand-binding, or immunoreactive polypeptides of this invention.

Functionally active polypeptides with altered enzymatic, binding, or immunoreactive properties can also be produced by altering the nucleotide sequence of a polynucleotide sequence that encodes a biologically active polypeptide of this invention. For example, by site directed mutagenesis, one can alter the nucleotide sequence of an expressed polypeptide and thereby introduce changes in the resulting expressed amino acid residue sequence. Thus, one can take a known polynucleotide and randomly alter it by random mutagenesis, reintroduce the altered polynucleotide into an expression system, and subsequently screen the product polypeptide for a desired property or activity.

Site-directed and random mutagenesis methods are well known in the polynucleotide arts, and are not to be construed as limiting as methods for altering the nucleotide sequence of a subject polynucleotide.

Due to the presence of the phage particle in an immunoaffinity or activity isolated polypeptide, one embodiment involves the manipulation of the resulting cloned genes to truncate the polypeptide encoding-gene such that a monomeric polypeptide is produced by the host *E. coli* cell containing the phage vector. Thus, the resulting manipulated cloned polypeptide encoding-genes produce a monomeric polypeptide which assemble to form a multimeric complex and can be readily characterized in ELISA assays for ligand-binding studies, in competition assays with known antagonists, and in enzymatic assays. The soluble monomer provides a reproducible and comparable preparation for comparative and characterization studies.

Alternative embodiments for practicing the invention are summarized hereafter in several formats to emphasize different aspects.

The method of producing a lambdoid bacteriophage comprises the steps of:
1) infecting a suitable suppressor host with an engineered lambdoid phage vector of this invention that encodes a fusion protein; and
2) culturing the host under phage growth conditions to express and assemble phage.

The method of producing a lambdoid bacteriophage can alternatively comprise the steps of:
1) introducing a preselected gene encoding a biologically active domain of a cytoplasmic protein into a cistron on a vector of this invention adapted for forming a fusion protein and monomeric proteins; and
2) expressing the vector in a suitable host to form assembled phage particles.

Preferably, the suppressor host has a termination codon suppressor phenotype selected from the group consisting of the amber and opal phenotypes. In addition, a preferred *E. coli* host strain is selected from the group consisting of strains EQ166, CA168 and MC8.

An alternative embodiment uses a separate cistron to express the wild-type phage surface protein, either on the same genome, on a second helper phage genome, or on any other recombinant molecule expressed in the host. Additionally, the separate cistron can be used to supplement the expression of the suppressor cistron to vary the ratio of fusion protein to monomer protein.

Another alternative embodiment uses a separate cistron to express the fusion protein, either on the same genome, on a second helper phage genome, or on any other recombinant molecule expressed in the host.

An additional alternative embodiment uses a separate cistron to express the monomeric protein, either on the same genome, on a second helper phage genome, or on any other recombinant molecule expressed in the host.

H. Expression Vectors and Polynucleotides for Expressing Proteins on the Surface of Lambda Phase Particles The preparation of bacteriophage lambda phage particles which display a functionally active protein on their surface depends, in one embodiment, on the cloning and expression vectors used to prepare the phage particles described herein.

A recombinant bacteriophage lambda vector of this invention produces fusion proteins that assemble with monomeric proteins to form a functionally active multimeric protein displayed on the surface of an assembled lambdoid phage particle.

A vector of the present invention is a recombinant DNA (rDNA) molecule adapted for receiving and expressing translatable DNA sequences in the form of a fusion polypeptide and a monomeric polypeptide. The said fusion polypeptide containing a lambdoid phage matrix anchor domain, a linker polypeptide, and a monomeric polypeptide. The vector comprises a cassette that includes upstream and downstream translatable DNA sequences operatively linked via a sequence of nucleotides adapted for ligation to an insert DNA. The upstream translatable sequence encodes the lambdoid phage matrix anchor domain and linker peptide as defined herein. The cassette preferably includes DNA expression control sequences for expressing the fusion polypeptide that is produced when an insert translatable DNA sequence (insert DNA) is inserted into the cassette via the sequence of nucleotides adapted for ligation. The lambdoid phage matrix anchor is preferably a portion of the pV tail protein capable of binding the matrix of a lambdoid phage particle, thereby incorporating the fusion polypeptide onto the phage surface.

The cassette preferably includes DNA expression control sequences for expressing the monomeric polypeptide that is produced when an insert translatable DNA sequence (insert DNA) is directionally inserted into the cassette via the sequence of nucleotides adapted for ligation. The monomeric polypeptide is preferably capable of associating with the fusion protein and other monomeric polypeptides, as required, thereby incorporating the monomeric polypeptide onto the phage surface. The fusion protein and monomeric proteins thus form a biologically active multimeric complex on the surface of the phage particle.

In addition, the cassette preferably includes DNA expression control sequences for expressing the fusion protein. The DNA expression control sequences for expressing the lambdoid phage matrix anchor are upstream and downstream of the nucleotide sequence encoding said lambdoid phage matrix anchor. The upstream DNA expression control sequences can be those found in any lambdoid phage and are regulated by proteins expressed by the lambdoid genome. The downstream DNA expression control sequence is a suppressor codon at the fusion point for conditional regulation of a read-through (fusion) product. The suppressor codon provides a means for the conditional expression of the lambdoid phage matrix anchor and the fusion product which comprises the lambdoid phage matrix anchor polypeptide, linker polypeptide, and downstream insert translatable DNA sequences. The lambdoid phage matrix anchor polypeptide is preferably capable of assembling with other lambdoid phage polypeptides to form a functional lambdoid phage tail, thereby providing the means for infection of a suitable bacterial host.

An expression vector is characterized as being capable of expressing, in a compatible host, structural gene products such as a fusion polypeptide and a lambdoid phage matrix anchor gene product of the present invention. In one embodiment, an expression vector is also characterized as being capable of expressing, in a compatible host, a heterologous monomeric gene product such as a monomeric polypeptide of the present invention for association with the fusion protein to form a multimeric protein complex in the phage matrix.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked.

As used herein with regard to DNA sequences or segments, the phrase "operatively linked" means the sequences or segments have been covalently joined, preferably by conventional phosphodiester bonds, into one strand of DNA, whether in single or double stranded form.

The choice of vector to which a cassette of this invention is operatively linked depends directly, as is well known in the art, on the functional properties desired, e.g., vector replication and protein expression, and the host cell to be transformed, these being limitations inherent in the art of constructing recombinant DNA molecules.

In preferred embodiments, the vector utilized includes a prokaryotic replicon i.e., a DNA sequence having the ability to direct autonomous replication and maintenance of the recombinant DNA molecule extra chromosomally in a prokaryotic host cell, such as a bacterial host cell, transformed therewith. Such replicons are well known in the art. Vectors typically also contain convenient restriction sites for insertion of translatable DNA sequences. Exemplary vectors are the lambda vectors EMBL3, EMBL4, FIX, FIX® II, DASH, DASH® II, ZAP, ZAP® II, and ZAP Express™ available from Stratagene (La Jolla, Calif.) and ExCell available from Pharmacia, (Piscataway, N.J.). In addition, embodiments may also include the α-peptide of the β-gal gene to facilitate the identification of recombinant vectors containing insert DNAs.

A sequence of nucleotides adapted for ligation, i.e., a polylinker or multiple cloning site (mcs), is a region of the DNA expression vector that (1) operatively links for replication the upstream and downstream translatable DNA sequences and (2) provides a site or means for insertion of a DNA sequence into the vector. Typically, a polylinker is a sequence of nucleotides that defines two or more restriction endonuclease recognition sequences, or restriction sites. Upon restriction cleavage, the site yields cohesive termini to which a translatable DNA sequence can be ligated to the DNA expression vector. In addition, a polylinker can be cleaved with two restriction endonucleases to form two cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, in a sequence that encodes a linker polypeptide, in a downstream translatable DNA sequence, or in two or more such sequences. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

A translatable DNA sequence is a linear series of nucleotides that provide an uninterrupted series of at least 8 codons that encode a polypeptide in one reading frame.

An upstream translatable DNA sequence encodes a lambdoid phage matrix anchor (tail polypeptide). Preferred matrix anchors are obtainable from lambdoid phage λ, Ø80, Ø81, and the like equivalent lambdoid phage. Preferred matrix anchor domains are found in the coat or tail proteins encoded by gene D and genes V and J, respectively. Thus, an upstream translatable DNA sequence encodes an amino acid residue sequence that corresponds, and preferably is identical, to the matrix anchor domain of either a lambdoid phage coat or tail protein. The matrix anchor domain of a lambdoid phage tail protein, pV, is preferably a portion of the amino terminal region of the tail protein and includes a region of amino acid residue sequences 1 to 176. pV tail protein is present on a mature lambdoid phage along the tail with typically about 192 copies of the tail protein.

A cassette in a DNA expression vector of this invention is the region of the vector that forms, upon insertion of a translatable DNA sequence (insert DNA), a sequence of nucleotides capable of expressing, in an appropriate host, a fusion polypeptide of this invention.

The expression-competent sequence of nucleotides is referred to as a cistron. Thus, the cassette comprises DNA expression control elements operatively linked to the upstream and downstream translatable DNA sequences. A cistron is formed when a translatable DNA sequence is directionally inserted (directionally ligated) between the upstream and downstream sequences via the sequence of nucleotides adapted for that purpose. The resulting translatable DNA sequences, namely the upstream and the inserted sequences, are all operatively linked in the same reading frame.

DNA expression control sequences comprise a set of DNA expression signals for expressing a gene product and include both 5' and 3' elements, as is well known, operatively linked to the cistron such that the cistron is able to express a gene product. The 5' control sequences define a promoter for initiating transcription and a ribosome binding site operatively linked at the 5' terminus of the upstream translatable DNA sequence.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine et al., *Nature*, 254:34, 1975). Alternatively, the initiation codon in *E. coli* may be GUG. The sequence, AGGAGGU, which is called the Shine-Dalgarno (SD) sequence, is complementary to the 3' end of *E. coli* 16S mRNA. Binding of the ribosome to mRNA and the sequence at the 3' end of the mRNA can be affected by several factors:

(i) The degree of complementarity between the SD sequence and 3' end of the 16S tRNA.

(ii) The spacing and possibly the DNA sequence lying between the SD sequence and the initiator codon (Roberts et al., *Proc. Natl. Acad. Sci. USA*, 76:760, 1979a; Roberts et al., *Proc. Natl. Acad. Sci. USA*, 76:5596, 1979b; Guarente et al., *Science*, 209:1428, 1980; and Guarente et al., *Cell*, 20:543, 1980). Optimization is achieved by measuring the level of expression of genes in plasmids in which this spacing is systematically altered. Comparison of different mRNAs shows that there are statistically preferred sequences from positions −20 to +13 (where the A of the AUG is position 0) (Gold et al., *Annu. Rev. Microbial.*, 35:365, 1981). Leader sequences have been shown to influence translation dramatically.

(iii) The nucleotide sequence following the initiator codon, which affects-ribosome binding (Taniguchi et al., *J. Mol. Biol.*, 118:533, 1978).

The 3' control sequences define at least one termination (stop) codon in frame with and operatively linked to the inserted translatable DNA sequence. The preferred stop codon is a suppressor codon that is regulated by conditional suppression. Conditional suppression refers to the use of nonsuppressor and suppressor hosts to express the encoded polypeptide under different conditions. In a nonsuppressor host, a tRNA does not insert an amino acid residue at the position of the amber codon resulting in termination of translation of the upstream lambda phage matrix anchor polypeptide. In a suppressor host, a mutant tRNA inserts an amino acid residue at the position of the amber codon resulting in a read-through at the position of the amber codon and translation of the downstream nucleotide sequences. Read-through thus results in the expression of a fusion protein comprising the lambda matrix anchor protein, a linker polypeptide, and an inserted translatable DNA sequence. In addition, in a suppressor host, initiation of translation of the inserted translatable DNA sequence occurs from 5' expression control elements contained within the linker peptide and results in translation of the inserted translatable DNA sequence. Further discussion regarding conditional suppression is described herein. Thus, a DNA expression vector of this invention provides a system for inserting translatable DNA sequences into the cassette portion of the vector to produce a cistron capable of expressing a fusion polypeptide of this invention.

In one embodiment, a DNA expression vector provides a system for inserting (cloning) a translatable DNA sequence into a single cassette present in the vector, to form two cistrons for expressing two polypeptides. The two polypeptides expressed are (1) a fusion polypeptide and (2) a truncated phage tail polypeptide, each capable of associating in the phage matrix to form a functional phage particle. The fusion polypeptide is formed in a suppressor host which allows conditional (partial) read-through of the suppressor termination codon, and the truncated tail polypeptide is formed where read-through does not occur and termination occurs at the suppressor termination codon.

In another embodiment, a DNA expression vector provides a system for inserting (cloning) a translatable DNA sequence into a single cassette present in the vector, to form three cistrons for expressing three polypeptides. Two of said polypeptides assemble to form a multimeric complex. The two polypeptides expressed are a fusion polypeptide and a monomeric polypeptide capable of associating to form a multimeric protein. The monomeric polypeptide is translated by initiation of translation using a second ribosome-binding-site located in the sequence defining the linker polypeptide. The third polypeptide in this embodiment is the truncated phage tail polypeptide produced by termination at the suppressor termination codon as discussed above.

Alternatively, a DNA expression vector of this invention can comprise, in addition to the cassette previously described in detail, a second cassette for expressing a monomeric polypeptide. The second cassette includes a sequence of nucleotides adapted for directional ligation to a downstream DNA sequence of the vector that typically defines at least one stop codon in the reading frame of the cassette. The second cassette includes a translatable DNA sequence encoding the monomeric polypeptide and is operatively linked at its 5' terminus to DNA expression control sequences forming the 5' elements defined above. A ribosome binding site of the second cassette is also contained within the 5' control elements of the polypeptide linker described herein. The second cassette is capable, upon insertion of a translatable DNA sequence (insert DNA), of expressing the monomeric polypeptide.

In another alternative embodiment, the second cassette for expressing monomeric polypeptide can be contained on a separate vector independent of the vector containing the cistron that encodes the fusion protein.

In a preferred embodiment, a DNA expression vector is designed for convenient manipulation in the form of a lambdoid phage particle encapsulating a genome according to the teachings of the present invention. In this embodiment, a DNA expression vector further contains a nucleotide sequence that defines a lambdoid phage origin of replication such that the vector can replicate as a lambdoid phage in double stranded replicative form and be packaged into lambdoid phage particles. This feature provides the ability of the DNA expression vector to be packaged into phage particles for subsequent segregation of the particle, and vector contained therein, away from other particles that comprise a population of phage particles.

A lambdoid phage origin of replication is a region of the phage genome, as is well known, that defines sites for initiation of replication and termination of replication.

A preferred lambdoid phage origin of replication for use in the present invention is a λ, Ø80, or Ø81 phage origin of replication. Particularly preferred is a lambdoid phage origin of replication described herein the Examples. Preferred DNA expression vectors are the expression vectors λV'sac, λV'mcs, λblue, λblue-α, and λfoo described in Example 1.

Insofar as a vector of this invention may be manipulated to contain an insert DNA, thereby having the capacity to express a fusion polypeptide and a monomeric polypeptide, one embodiment contemplates the previously described vectors containing an insert DNA. Particularly preferred vectors containing multimeric protein genes are described in the Examples.

In preferred embodiments, the vector utilized is capable of replication in a suitable procaryotic host cell and includes a prokaryotic origin of replication or replicon, i.e., a DNA sequence having the ability to direct autonomous replication and maintenance of the recombinant DNA molecule extra chromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is the λori.

Alternatively, the vector utilized includes sequences encoding gene products that promote insertion of the recombinant DNA molecule into the DNA of the prokaryotic host-cell, such as a bacterial host cell, transformed therewith. The vector utilized also includes sequences encoding gene products that promote the maintenance of insertion of the recombinant DNA molecule in the DNA of the prokaryotic host cell, such as a bacterial host cell, transformed therewith. The recombinant DNA molecule so inserted replicates as part of the prokaryotic host cell chromosome. This process of insertion, maintenance, and replication is known as lysogenization. Such gene products that promoter lysogenization are well known in the art. Preferred gene products which promote lysogenization are those that are efficient in the host organism. A preferred host cell is *E. coli*. Preferred gene products are those expressed by λ.

A vector for expression of a functionally active protein of the invention on the surface of a lambdoid phage particle is a recombinant DNA (rDNA) molecule adapted for receiving and expressing translatable DNA sequences.

In one embodiment, the expressed translatable DNA sequence is a monomer of a multimeric protein. The rDNA molecule of this invention is capable of expressing the translatable DNA sequence as a fusion polypeptide fused to a portion of a lambdoid matrix anchor protein. That is, one of the polypeptides expressed is a fusion polypeptide comprising a lambdoid phage matrix anchor polypeptide, linker polypeptide, and a preselected monomer polypeptide.

A DNA expression vector for expressing a functionally active molecule provides a system for cloning (inserting) a translatable DNA sequence into a cassette present in the vector, to form three separate cistrons for expressing the first, second, and third polypeptides of the functionally active molecule, or the phage tail polypeptide, fusion polypeptide, and monomeric polypeptide that comprise the phage tail molecule and multimeric molecule. The DNA expression vector for expressing three cistrons is referred to as a tricistronic expression vector.

A DNA expression vector of the present invention provides translatable DNA sequences comprising a linker polypeptide. The linker polypeptide can provide several features which include: 1) a suppressor codon, 2) translatable DNA sequences comprising a flexible amino acid sequence and a proteolytic cleavage site, 3) a DNA expression control element for expression of the downstream translatable insert DNA, and 4) a sequence of nucleotides adapted for ligation to an insert DNA.

The suppressor codon allows for the expression of the fusion polypeptide described herein in a suitable suppressor host. In a nonsuppressor host, the suppressor codon allows for the translational termination of the upstream DNA translatable sequence.

The linker polypeptide can also provide a means for control of DNA expression of the downstream polypeptide. The 5' control sequences define a ribosome binding site which is operatively linked at the 5' terminus of the downstream polypeptide. The ribosome binding site is linked to the cistron such that the cistron is able to express a structural gene product.

The translatable DNA sequences which encode the linker polypeptide also provide a means for ligation of an insert DNA into the expression vector.

A preferred recombinant bacteriophage lambda vector is a recombinant DNA (rDNA) molecule comprising a nucleotide sequence that (i) defines the lambdoid elements for replication and packaging of the vector into an assembled bacteriophage as described herein, and (ii) encodes a conditionally suppressible cistron for expression of both a tail protein and a fusion protein. The conditionally suppressible cistron comprises:
  a) a promoter for transcribing the cistron operatively linked 5' to the reading frame of the cistron,
  b) a first upstream translatable sequence that encodes a lambdoid bacteriophage tail polypeptide,
  c) a first ribosome binding site to initiate translation of the upstream translatable sequence,
  d) a second translatable sequence operatively linked downstream to the first translatable sequence that (i) encodes a linker polypeptide in frame with tail polypeptide and (ii) includes a sequence adapted for ligation of an insert polynucleotide that defines a third translatable sequence downstream from the second translatable sequence that encodes a preselected polypeptide, and e) a suppressor termination codon within the second translatable sequence that upon suppression results in read-through to form a fusion polypeptide consisting of the tail polypeptide, linker polypeptide and preselected polypeptide.

In this embodiment, upon insertion of a insert polynucleotide that encodes a preselected polypeptide to be displayed on the fusion protein into the sequence adapted for ligation, the vector can produce two proteins when grown in a conditional suppressor host strain that partially suppresses termination, resulting is a ratio of two translation products. The two products are (1) a truncated tail protein produced by termination at the non-suppressed suppressor codon, and (2) a fusion protein comprising, in the direction of amino- to carboxy-terminus, a phage tail polypeptide domain, a linker polypeptide domain and a preselected polypeptide domain produced by suppression and read-through of the suppressor codon and translation of the third translatable sequence. Thus, the degree of suppression controls the ratio of the two products produced by the cistron in the vector.

This embodiment has the advantage of providing both the fusion protein and the bacteriophage tail protein. By selection of the suppressor host properly, the ratio can be adjusted such that read-through is a rare event, yielding 1 to 10 copies of fusion protein to 200 copies of the truncated tail protein. A single vector can thereby produce all the tail components required for assembly of infectious lambdoid bacteriophage including the proper amount of fusion protein.

In a related embodiment, the vector can further contain a nucleotide sequence that defines a second ribosome binding site in the above described second translatable sequence (linker polypeptide domain) that initiates translation of the third translatable sequence, i.e., the preselected polypeptide as a free non-fused polypeptide. Thus, the same vector that produced the above two polypeptides, namely the truncated tail protein and the fusion protein, can also produce a third protein by initiation of translation at the second ribosome binding site to produce the preselected polypeptide as a free protein rather that as a portion of the fusion protein.

This embodiment provides the advantage of producing the monomer subunits of the preselected polypeptide of a multimer in addition to the fusion protein subunit of the multimer.

A preferred nucleotide sequence in the first upstream translatable sequence that encodes a tail polypeptide encodes any of the lambdoid tail proteins, preferably selected from the group consisting of pJ, pV, pG, pM and pT. A particularly preferred tail protein is pM, and more preferably, the fusion protein includes residues 1-176 of the sequence of pV shown in SEQ ID NO 1, or conservative substitutions thereof.

A preferred suppressor termination codon is either the amber or opal codons, and depends upon the suppressor strain to be utilized in conjunction with the vector, as is described herein.

A preferred second translatable sequence that defines a linker can be any sequence that encodes a linker as described herein, and preferably includes the sequence adapted for ligation (a multiple cloning site or sites), preferably directional ligation. A preferred linker polypeptide is the Pro-Thr box of C. fimi endoglucanase and exoglucanase as described herein. An additional preferred linker is described in the Examples and has a nucleotide sequence from base number 547 to 654 of SEQ ID NO 5.

A cassette in a DNA expression vector of this invention is the region of the vector that forms, upon insertion of a translatable DNA sequence (insert DNA), a sequence of nucleotides capable of expressing, in an appropriate host, a polypeptide. The expression-competent sequence of nucleotides is referred to as a cistron. Thus, the cassette comprises DNA expression control elements operatively linked to the upstream translatable DNA sequences. A cistron is formed when a translatable DNA sequence is inserted (ligated) into the expression vector via the sequence of nucleotides adapted for that purpose. The resulting three translatable DNA sequences, namely the first upstream, the second upstream (linker) and the inserted sequences, are all operatively linked.

In so far as promoters in prokaryotes may control transcription of large polycistronic messenger RNA molecules, the promoter in the present vector can be positioned at any of a variety of locations in the lambdoid genome and need not be immediately adjacent to the 5' ribosome binding site that initiates translation of the cistron that encodes the fusion protein of this invention.

Thus, a DNA expression vector for expressing a phage tail polypeptide, a fusion polypeptide, and optionally a monomeric polypeptide provides a system for cloning preselected translatable DNA sequences into the cassette portions of the vector to produce cistrons capable of expressing the first and second, and optionally third polypeptides, e.g., the pV, the pV-monomer (fusion polypeptide), and monomer polypeptides. The fusion and monomer polypeptides assemble to form a multimeric protein.

Insofar as polynucleotides are component parts of a DNA expression vector for producing a fusion polypeptide residue sequence, the invention also contemplates isolated polynucleotides that encode such fusion sequences.

It is to be understood that, due to the genetic code and its attendant redundancies, numerous polynucleotide sequences can be designed that encode a contemplated pV residue sequence. Thus, the invention contemplates such alternate polynucleotide sequences incorporating the features of the redundancy of the genetic code.

Insofar as the expression vector for producing a fusion polypeptide of this invention is carried in a host cell compatible with expression of the fusion polypeptide, the invention contemplates a host cell containing a vector or polynucleotide of this invention. A preferred host cell is E. coli, as described herein.

An E. coli host, MC8, capable of replicating and expressing the preferred expression vector of this invention, was deposited pursuant to Budapest Treaty requirements with the American Type Culture Collection (ATCC), Rockville, Md., as described herein. Lambdoid genomic DNA, γfoo, comprising a preferred expression vector that produces a fusion polypeptide of this invention was deposited pursuant to Budapest Treaty requirements with the American Type Culture Collection (ATCC), Rockville, Md., as described herein.

1. Multimer Configurations

A particularly preferred cistron that encodes a lambda pV tail polypeptide, a preferred linker, and a second translatable sequence that encodes the linker together with a sequence adapted for ligation of an insert DNA and the α-peptide of β-gal is shown in SEQ ID NO 5. This cistron includes two additional overlapping cistrons that encode a lambda truncated tail polypeptide produced by termination at the non-suppressed suppressor codon (from base number 1 to 545 of SEQ ID NO 5) and a sequence adapted for ligation of an insert polynucleotide that defines a third translatable sequence that encodes a preselected polypeptide (from base number 643 to 728 of SEQ ID NO 5).

The invention can be practiced so as to produce a monomer fusion protein, but is particularly suited for expression of multimers: homomultimers and heteromultimers which assemble in the cytoplasm. To that end, the cistrons which express the subunits can be located within the fusion protein cistron, i.e., overlapping, or can be a second non-overlapping cistron. In this latter configuration, the monomer can be a polypeptide different from the fusion protein's preselected polypeptide, and can be used to form heteromultimers. The cistron for expression of the different polypeptides can be located in cis or trans relative to the fusion protein cistron.

I. Libraries of Phage

The present invention contemplates a library of DNA molecules that each encode a fusion protein of this invention where the library is in the form of a population of different lambdoid phage particles each containing a different rDNA molecule of this invention. By different rDNA molecule is meant rDNA molecules differing in nucleotide base sequence encoding the preselected polypeptide of the fusion protein.

Thus, a phage library is a population of lambdoid phage, preferably λ, Ø80, or Ø81 lambdoid phage, each phage having packaged inside the particle a rDNA expression vector of this invention. A preferred library is comprised of phage particles containing DNA molecules that encode at least $10^6$, preferably $10^7$ and more preferably $10^{8-9}$ different fusion proteins of this invention. By different fusion proteins is meant fusion proteins differing in amino acid residue sequence. Where the packaged expression vector encodes polypeptides of an autogenously assembling receptor, e.g. β-gal or BPA monomers that assemble to form a biologically active enzyme or lectin, respectively; the library can also be characterized as containing or expressing a multiplicity of receptor specificities. Thus, preferred libraries express at least $10^5$, preferably at least $10^6$ and more preferably at least $10^7$ different receptors, such as different enzymes, lectins, and the like.

As described herein, a particular advantage of a lambdoid phage in the present invention is that the DNA molecule present in the phage particle and encoding the multimeric receptor can be segregated from other DNA molecules present in the library on the basis of the presence of the particular expressed fusion protein on the surface of the phage particle.

Isolation (segregation) of a DNA molecule encoding one or more members of a multimeric receptor is conducted by segregation of the lambdoid phage particle containing the gene or genes of interest away from the population of other phage particles comprising the library. Segregation of phage particles involves the physical separation and propagation of individual phage particles away from other particles in the library. Methods for physical separation of lambdoid phage particles to produce individual particles, and the propagation of the individual particles to form populations of progeny phage derived from the individual segregated particle are well known in the lambdoid phage arts.

A preferred separation method involves the identification of the expressed multimer on the surface of the phage particle by means of substrate- or ligand-binding specificity between the phage particle and a preselected substrate or ligand. Exemplary and preferred is the use of "panning" methods whereby a suspension of phage particles is contacted with a solid phase substrate or ligand and allowed to specifically bind. After binding, non-bound particles are washed off the solid phase, and the bound phage particles are those that contain substrate- or ligand-specific multimeric receptor (homotetramer) on their surface. The bound particles can then be recovered by elution of the bound particle from the solid phase, typically by the use of a protease which provides a means for the separation of the phage particle containing the recombinant genome and the multimeric receptor. An alternative method for recovering the bound particles by elution of the bound particle from the solid phase is by the use of aqueous solvents having high ionic strength sufficient to disrupt the receptor-ligand or receptor-substrate binding interaction.

An alternate method for separating a phage particle based on the ligand specificity of the surface-expressed multimer from a population of particles is to precipitate the phage particles from the solution phase by crosslinkage with the ligand. Such methods are well known in the immunological arts.

The use of the above particle segregation methods provides a means for screening a population of lambdoid phage particles present in a phage library of this invention. As applied to a phage library, screening can be utilized to enrich the library for one or more particles that express a multimer having a preselected substrate or ligand binding specificity. Where the library is designed to contain multiple species of multimers that all have some detectable measure of ligand binding activity, but differ in protein structure, ligand binding affinity or avidity, and the like, the screening methods can be utilized sequentially to first produce a library enriched for a preselected binding specificity, and then to produce a second library further enriched by further screening comprising one or more isolated phage particles. Methods for measuring ligand binding activities, and the like interactions between a ligand and a receptor are generally well known and are not discussed further as they are not essential features of the present invention.

Thus, in one embodiment, a phage library is a population of particles enriched for a preselected ligand binding specificity.

In another embodiment, a phage library comprises a population of particles wherein each particle contains at least one fusion protein of this invention on the surface of the phage particle. The actual amount of fusion protein present on the surface of a phage particle depends, in part, on the choice of coat protein membrane anchor present in the fusion protein. Where the anchor is derived from pD, there is the potential for hundreds of fusion proteins on the particle surface depending on the growth conditions and other factors. Where the anchor is derived from the more preferred pV, there are typically about 1 to 4 fusion proteins per phage particle. Preferably, a phage particle in a library contains from about 1 to about 10 pV-derived fusion proteins on the surface of each particle, and more preferably about 1 to 5 fusion proteins per particle. Exemplary amounts of surface fusion protein are shown by the electron micrographs described in the Examples that describe particles having about 1 to 3 pV-derived fusion proteins per particle.

In another embodiment, the present invention contemplates a population of phage particles that are the progeny of a single particle, and therefor all express the same multimer on the particle surface. Such a population of phage are homogeneous and clonally derived, and therefore provide a source for expressing large quantities of a particular fusion protein.

1. Methods for Producing a Library a. General Rationale

The present invention provides a system for the simultaneous cloning and screening of preselected substrate- or ligand-binding specificities or preselected biological activity specificities from gene libraries using a single vector system. This system provides linkage of cloning and screening methodologies and has two requirements. First, that expression of the polypeptide chains of a multimeric protein complex in an in vitro expression host such as E. coli requires expression of the monomeric polypeptide chains in order that a functional multimeric receptor can assemble to produce a complex that has a desired biological function. Second, that screening of isolated members of the library for a preselected biological activity requires a means to correlate (a linkage) the activity of an expressed molecules with a convenient means to isolate the gene that encodes the member from the library.

Linkage of expression and screening is accomplished by the combination of expression of a fusion polypeptide in the cytoplasm of a bacterial cell to allow assembly of a functional complex, and the targeting of a fusion polypeptide onto the tail of a lambdoid phage particle during phage assembly to allow for convenient screening of the library member of interest. Targeting to a phage particle is provided by the presence of a lambdoid phage tail protein matrix anchor domain (i.e., a pV-derived matrix anchor domain) in a fusion polypeptide of this invention.

The present invention contemplates in one embodiment a method for producing a library of DNA molecules, each DNA molecule comprising a cistron for expressing a fusion polypeptide on the surface of a lambdoid phage particle. The method comprises the steps of (a) forming a ligation admixture by combining in a ligation buffer (i) a population of preselected polypeptide encoding genes and (ii) a plurality of DNA expression vectors in linear form adapted to form fusion polypeptide- and pV polypeptide-expressing cistrons, and (b) subjecting the admixture to ligation conditions for a time period sufficient for the library of genes to become operatively linked (ligated) to the plurality of vectors to form the library.

In this embodiment, the library of polypeptide encoding genes are in the form of double-stranded (ds) DNA and each member of the population has cohesive termini adapted for ligation. In addition, the plurality of DNA expression vectors are each linear DNA molecules having upstream and downstream cohesive termini that are (a) adapted for receiving the polypeptide genes, and (b) operatively linked to respective upstream and downstream translatable DNA sequences. The upstream translatable DNA sequence encodes a lambdoid phage tail protein matrix anchor, preferably a portion of the pV polypeptide preceding a linker polypeptide as described herein for a polypeptide of this invention. The downstream translatable DNA sequence encodes a preselected polypeptide. The translatable DNA sequences are also operatively linked to respective upstream and downstream DNA expression control sequences as defined for a DNA expression vector described herein.

The library so produced can be utilized for expression and screening of the assembled fusion polypeptide and monomeric polypeptides encoded by the resulting library of cistrons represented in the library by the expression and screening methods described herein.

2. Production of Gene Libraries

A gene library is a collection of different genes, preferably polypeptide-encoding genes (polypeptide genes), and may be isolated from natural sources or can be generated artificially. Preferred gene libraries comprise genes that code for the members of a monomeric or multimeric molecule of interest.

A gene library useful in practicing the present invention contains at least $10^3$, preferably at least $10^4$, more preferably at least $10^5$, and most preferably at least $10^7$ different genes. Methods for evaluating the diversity of a library of genes is well known to one skilled in the art.

Thus, in one embodiment, the present invention contemplates a method of isolating genes coding for a multimeric protein complex having a preselected activity from a collection of genes. Additionally, expressing the cloned genes and isolating the resulting expressed multimeric protein complex is also described. Preferably, the complex will be a multimeric polypeptide capable of binding a ligand, such as a cytoplasmic an enzyme or lectin of interest.

Various well known methods can be employed to produce a useful gene library. In some cases, it is desirable to bias a library for a preselected activity, such as by using as a source of nucleic acid cells (source cells) at various stages of age, health, stimulation, or disease state.

In addition, a library of diverse nucleotide sequences can be produced by directed or random mutagenesis of a preselected gene or population of genes. Methods of mutagenesis are well known and are not to be considered limiting to the present invention.

Alternatively, it should be noted that the greater the genetic heterogeneity of the population of cells from which the nucleic acids are obtained, the greater the diversity of the library that will be made available for screening according to the method of the present invention. Thus, cells from different individuals and cells from different strains, races or species can be advantageously combined to increase the heterogeneity (diversity) or a library.

Methods for preparing fragments of genomic DNA from which genes can be cloned as a diverse population are well known in the art. See for example Herrmann et al., *Methods In Enzymol.*, 152:180-183, 1987; Frischauf, *Methods In Enzymol.*, 152:183-190, 1987; Frischauf, *Methods In Enzymol.*, 152:190-199, 1987; and DiLella et al., *Methods In Enzymol.*, 152:199-212, 1987).

The desired polypeptide-encoding genes can be isolated from either genomic material containing the gene expressed or the messenger RNA (mRNA) which represents a transcript comprising the coding region of the gene. The difficulty in using the genomic DNA is in juxtaposing the sequences coding for polypeptides, where the sequences are separated by introns. The DNA fragment(s) containing the proper exons must be isolated, the introns excised, and the exons then spliced in the proper order and in the proper orientation. For the most part, this will be difficult, so that the alternative technique employing the isolation of mRNA will be the method of choice because the coding regions of the gene have translocated to become adjacent, so that the sequence is continuous (free of introns) for the entire polypeptide-coding regions.

Where mRNA is utilized the cells will be lysed under Rnase inhibiting conditions. In one embodiment, the first step is to isolate the total cellular mRNA. Poly $A^+$ mRNA can then be selected by hybridization to an oligo-dT cellulose column.

a. Preparation of Polynucleotide Primers

The term "polynucleotide" as used herein in reference to primers, probes and nucleic acid fragments or segments to be synthesized by primer extension is defined as a molecule comprised of two or more deoxyribonucleotide or ribonucleotides, preferably more than 3. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and Ph. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on may factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarily with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., *Nucl. Acids Res.*, 12:7057-70, 1984; Studier et al., *J. Mol. Biol.*, 189:113-130, 1986; and *Molecular Cloning: A Laboratory Manual. Second Edition*, Maniatis et al., eds., Cold Spring Harbor, N.Y., 1989.

When a primer containing a DNA-dependent RNA polymerase promoter is used the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi et al., *Biotechnology*, 6:1197-1202, 1988. RNA-directed polymerases produce large numbers of RNA strands from a small number of template RNA strands that contain a template sequence or replication initiation site. These polymerases typically give a one million-fold amplification of the template strand as has been described by Kramer et al., *J. Mol. Biol.*, 89:719-736, 1974.

The polynucleotide primers can be prepared using any suitable method, such as, for example, the phosphotriester or phosphodiester methods see Narang et al., *Meth. Enzymol.*, 68:90, 1979; U.S. Pat. No. 4,356,270; and Brown et al., *Meth. Enzymol.*, 68:109, 1979.

The choice of a primer's nucleotide sequence depends on factors such as the distance on the nucleic acid from the region coding for the desired receptor, its hybridization site on the nucleic acid relative to any second primer to be used, the number of genes it is to hybridize to, and the like.

1) Primers for Producing Gene Libraries

Gene libraries can be prepared prior to their utilization in the present invention. Library preparation is typically accomplished by primer extension, preferably by primer extension in a cDNA format.

To produce a collection of DNA homologs by primer extension, the nucleotide sequence of a primer is selected to hybridize with a plurality of genes at a site defined by the addition of multiple poly(A)s in the 3' untranslated region of the mRNA (polyA tail) so that a nucleotide sequence coding for a functional (capable of binding) polypeptide is obtained. To hybridize to a plurality of different nucleic acid strands, the primer must be a substantial complement of a nucleotide sequence conserved among the different strands. Such sites include nucleotide sequences in the polyA tail and the like.

Alternatively, if the repertoires of conserved receptor DNA homologs are to be produced by (PCR) amplification, two primers, i.e., a PCR primer pair, must be used for each coding strand of nucleic acid to be amplified. The first primer becomes part of the nonsense (minus or complementary) strand and hybridizes to a nucleotide sequence conserved among receptor (plus or coding) strands within the repertoire. To produce receptor-coding DNA homologs, first primers are therefore chosen to hybridize to (i.e. be complementary to) conserved regions within the gene. Second primers become part of the coding (plus) strand and hybridize to a nucleotide sequence conserved among minus strands. To produce the receptor-coding DNA homologs, second primers are therefore chosen to hybridize with a conserved nucleotide sequence at the 5' end of the receptor-coding gene. It should be noted that in the amplification of receptor-coding DNA homologs the conserved 5' nucleotide sequence of the second primer can be complementary to a sequence exogenously added using terminal deoxynucleotidyl transferase as described by Loh et al., *Science*, 243:217-220, 1989. One or both of the first and second primers can contain a nucleotide sequence defining an endonuclease recognition site. The site can be heterologous to the receptor gene being amplified and typically appears at or near the 5' end of the primer.

When present, the restriction site-defining portion is typically located in a 5'-terminal non-priming portion of the primer. The restriction site defined by the first primer is typically chosen to be one recognized by a restriction enzyme that does not recognize the restriction site defined by the second primer, the objective being to be able to produce a DNA molecule having cohesive termini that are non-complementary to each other and thus allow directional insertion into a vector.

In one embodiment, the present invention utilizes a set of polynucleotides that form primers having a priming region located at the 3'-terminus of the primer. The priming region is typically the 3'-most (3'-terminal) 15 to 30 nucleotide bases. The 3'-terminal priming portion of each primer is capable of acting as a primer to catalyze nucleic acid synthesis, i.e., initiate a primer extension reaction off its 3' terminus. One or both of the primers can additionally contain a 5'-terminal (5'-most) non-priming portion, i.e., a region that does not participate in hybridization to the template.

In PCR, each primer works in combination with a second primer to amplify a target nucleic acid sequence. The choice of PCR primer pairs for use in PCR is governed by considerations as discussed herein for producing gene libraries. That is, the primers have a nucleotide sequence that is complementary to a sequence in the gene to be amplified.

2) Polymerase Chain Reaction to Produce Gene Libraries

The strategy used for cloning a preselected gene will depend, as is well known in the art, on the type, complexity, and purity of the nucleic acids making up the genes.

The preselected gene to be cloned is comprised of polynucleotide coding strands, such as mRNA and/or the sense strand of genomic DNA. If the gene is in the form of double stranded genomic DNA, it is usually first denatured, typically by melting, into single strands. A DNA-encoded gene is subjected to a PCR reaction by treating (contacting) the DNA with a PCR primer pair, each member of the pair having a preselected nucleotide sequence. The PCR primer pair is capable of initiating primer extension reactions by hybridizing to nucleotide sequences, preferably at least about 10 nucleotides in length and more preferably at least about 20 nucleotides in length. The first primer of a PCR primer pair is sometimes referred to herein as the "sense primer" because it hybridizes to the coding or sense strand of a nucleic acid. In addition, the second primer of a PCR primer pair is sometimes referred to herein as the "anti-sense primer" because it hybridizes to a non-coding or anti-sense strand of a nucleic acid, i.e., a strand complementary to a coding strand.

The PCR reaction is performed by mixing the PCR primer pair, preferably a predetermined amount thereof, with the nucleic acids, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing a plurality of different DNA homologs.

A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined to increase the diversity of the gene library.

In another strategy, the object is to clone a preselected gene by providing a polynucleotide complement of the genes, such as the anti-sense strand of genomic dsDNA or the polynucleotide produced by subjecting mRNA to a reverse transcriptase reaction. Methods for producing such complements are well known in the art.

The PCR reaction is performed using any suitable method. Generally it occurs in a buffered aqueous solution, i.e., a PCR buffer, preferably at a pH of 7-9, most preferably about 8. Preferably, a molar excess (for genomic nucleic acid, usually about $10^6$:1 primer:template) of the primer is admixed to the buffer containing the template strand. A large molar excess is preferred to improve the efficiency of the process.

The PCR buffer also contains the deoxyribo-nucleotide triphosphates dATP, dCTP, dGTP, and dTTP and a polymerase, typically thermostable, all in adequate amounts for primer extension (polynucleotide synthesis) reaction. The resulting solution (PCR admixture) is heated to about 90° C.-100° C. for about 1 to 10 minutes, preferably from 1 to 4 minutes. After this heating period the solution is allowed to cool to 48° C.-54° C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40° C. An exemplary PCR buffer comprises the following: 50 mM KCl; 10 mM Tris-HCl; pH 8.3; 1.5 mM $MgCl_2$; 0.001% (wt/vol) gelatin, 200 µM dATP; 200 µM dTTP; 200 µM dCTP; 200 µM dGTP; and 2.5 units *Thermus acuaticus* DNA polymerase I (U.S. Pat. No. 4,889,818) per 100 microliters of buffer.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., *The Enzymes*, ed. P. Boyer, PP. 87-108, Academic Press, New York, 1982. Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nuc. Acid Res.*, 17:711-722, 1989. Amplification systems based on transcription have been described by Gingeras et al., in *PCR Protocols, A Guide to Methods and Applications*, pp 245-252, Academic Press, Inc., San Diego, Calif., 1990.

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process.

The first and/or second PCR reactions discussed above can advantageously be used to incorporate into the gene a preselected epitope useful in immunologically detecting and/or isolating the protein expressed by the cloned gene. This is accomplished by utilizing a first and/or second polynucleotide synthesis primer or expression vector to incorporate a predetermined amino acid residue sequence into the amino acid residue sequence of the encoded protein.

After producing DNA homologs for a plurality of different genes, the DNA molecules are typically further amplified. While the DNA molecules can be amplified by classic techniques such as incorporation into an autonomously replicating vector, it is preferred to first amplify the molecules by subjecting them to a polymerase chain reaction (PCR) prior to inserting them into a vector. PCR is typically carried out by thermocycling i.e., repeatedly increasing and decreasing the temperature of a PCR reaction admixture within a temperature range whose lower limit is about 10° C. to about 40° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

PCR amplification methods are described in detail in U.S. Pat. Nos. 4,683,195, 4,683,202, 4,800,159, and 4,965,188, and at least in several texts including "PCR Technology: Principles and Applications for DNA Amplification", H. Erlich, ed., Stockton Press, New York, 1989; and "PCR Protocols: A Guide to Methods and Applications", Innis et al., eds., Academic Press, San Diego, Calif., 1990.

In preferred embodiments only one pair of first and second primers is used per amplification reaction. The amplification reaction products obtained from a plurality of different amplifications, each using a plurality of different primer pairs, are then combined.

However, the present invention also contemplates DNA homolog production via co-amplification (using two pairs of primers), and multiplex amplification (using up to about 8, 9 or 10 primer pairs).

In preferred embodiments, the PCR process is used not only to produce a library of DNA molecules, but also to induce mutations within the library or to create diversity from a single parental clone and thereby provide a library having a greater heterogeneity. First, it should be noted that the PCR process itself is inherently mutagenic due to a variety of factors well known in the art. Second, in addition to the mutation inducing variations described in the above referenced U.S. Pat. No. 4,683,195, other mutation inducing PCR variations can be employed. For example, the PCR reaction admixture, can be formed with different amounts of one or more of the nucleotides to be incorporated into the extension product. Under such conditions, the PCR reaction proceeds to produce nucleotide substitutions within the extension product as a result of the scarcity of a particular base. Similarly, approximately equal molar amounts of the nucleotides can be incorporated into the initial PCR reaction admixture in an amount to efficiently perform X number of cycles, and then cycling the admixture through a number of cycles in excess of X, such as, for instance, 2X.

Alternatively, mutations can be induced during the PCR reaction by incorporating into the reaction admixture nucleotide derivatives such as inosine, not normally found in the nucleic acids being amplified. During subsequent in vivo DNA synthesis and replication of the nucleic acids in a host cell, the nucleotide derivative will be replaced with a substitute nucleotide thereby inducing a mutation.

b. Production of Gene Libraries Using cDNA Synthesis

1) Preparation of RNA

Total cellular RNA is prepared from appropriate cells using the RNA preparation methods described by Chomczynski et al., Anal Biochem., 162:156-159, 1987 and using the RNA isolation kit (Stratagene) according to the manufacturer's instructions. Briefly, immediately after isolation of the cells, the cells are homogenized in 10 ml of a denaturing solution containing 4.0 M guanine isothiocyanate, 0.25 M sodium citrate at pH 7.0, and 0.1 M beta-mercaptoethanol using a glass homogenizer. One ml of sodium acetate at a concentration of 2 M at pH 4.0 is admixed with the homogenized spleen. One ml of phenol that has been previously saturated with $H_2O$ is also admixed to the denaturing solution containing the homogenized spleen. Two ml of a chloroform:isoamyl alcohol (24:1 v/v) mixture is added to this homogenate. The homogenate is mixed vigorously for ten seconds and maintained on ice for 15 minutes. The homogenate is then transferred to a thick-walled 50 ml polypropylene centrifuge tube (Fisher Scientific Company, Pittsburgh, Pa.). The solution is centrifuged at 10,000×g for 20 minutes at 4° C. The upper RNA-containing aqueous layer is transferred to a fresh 50 ml polypropylene centrifuge tube and mixed with an equal volume of isopropyl alcohol. This solution is maintained at −20° C. for at least one hour to precipitate the RNA. The solution containing the precipitated RNA is centrifuged at 10,000×g for twenty minutes at 4° C. The pelleted total cellular RNA is collected and dissolved in 3 ml of the denaturing solution described above. Three ml of isopropyl alcohol is added to the re-suspended total cellular RNA and vigorously mixed. This solution is maintained at −20° C. for at least 1 hour to precipitate the RNA. The solution containing the precipitated RNA is centrifuged at 10,000×g for ten minutes at 4° C. The pelleted RNA is washed once with a solution containing 75% ethanol. The pelleted RNA is dried under vacuum for 15 minutes and then re-suspended in dimethyl pyrocarbonate (DEPC) treated (DEPC-$H_2O$)$H_2O$.

Messenger RNA (mRNA) enriched for sequences containing long poly A tracts is prepared from the total cellular RNA using methods described in *Molecular Cloning: A Laboratory Manual*, Maniatis et al., eds., Cold Spring Harbor, N.Y., 1982. Briefly, one half of the total RNA isolated is re-suspended in one ml of DEPC-$H_2O$ and maintained at 65° C. for five minutes. One ml of 2× high salt loading buffer consisting of 100 mM Tris-HCl (Tris [hydroxymethyl]amino methane hydrochloride), 1 M sodium chloride (NaCl), 2.0 mM disodium ethylene diamine tetra-acetic acid (EDTA) at pH 7.5, and 0.2% sodium dodecyl sulfate (SDS) is added to the re-suspended RNA and the mixture allowed to cool to room temperature. The mixture is then applied to an oligo-dT (Collaborative Research Type 2 or Type 3) column that has been previously prepared by washing the oligo-dT with a solution containing 0.1 M sodium hydroxide and 5 mM EDTA and then equilibrating the column with DEPC-$H_2O$. The eluate is collected in a sterile polypropylene tube and reapplied to the same column after heating the eluate for 5 minutes at 65° C. The oligo dT column is then washed with 2 ml of high salt loading buffer consisting of 50 mM Tris-HCl, pH 7.5, 500 mM sodium chloride, 1 mM EDTA at pH 7.5 and 0.1% SDS. The oligo dT column is then washed with 2 ml of 1× medium salt buffer consisting of 50 mM Tris-HCl, pH 7.5, 100 mM, 1 mM EDTA and 0.1% SDS. The messenger RNA is eluted from the oligo dT column with 1 ml of buffer consisting of 10 mM Tris-HCl, pH 7.5, 1 mM EDTA, at pH 7.5, and 0.05% SDS. The messenger RNA is purified by extracting this solution with phenol/chloroform followed by a single extraction with 100% chloroform. The messenger RNA is concentrated by ethanol precipitation and re-suspended in DEPC $H_2O$.

The messenger RNA (mRNA) isolated by the above process contains a plurality of different polynucleotides, i.e., greater than about $10^4$ different genes. Thus, the mRNA population represents a repertoire of genes.

2) Preparation of DNA Homologs

In preparation for PCR amplification, mRNA prepared above is used as a template for cDNA synthesis by a primer extension reaction. In a typical 50 µl transcription reaction, 5-10 µg of mRNA in water is first hybridized (annealed) with 500 ng (50.0 pmol) of a 3' primer, at 65° C. for five minutes. Suitable 3' primers comprise primers designed to specifically anneal to a single mRNA transcript or those primers designed to anneal to multiple transcripts, e.g. polyT primers. Subsequently, the mixture is adjusted to 1.5 mM dATP, dCTP, dGTP and dTTP, 40 mM Tris-HCl, pH 8.0, 8 mM $MgCl_2$, 50 mM NaCl, and 2 mM spermidine. Moloney-Murine Leukemia virus Reverse transcriptase (Stratagene), 26 units, is added and the solution is maintained for 1 hour at 37° C.

PCR amplification is performed in a 100 µl reaction containing the products of the reverse transcription reaction (approximately 5 µg of the cDNA/RNA hybrid), 300 ng of 3' primer, 300 ng of the 5' primer, 200 mM of a mixture of dNTP's, 50 mM KCl, 10 mM Tris-HCl pH 8.3, 1.5 mM MgCl$_2$, 0.1% gelatin and 2.5 units of *Thermus acuaticus* (Taq) DNA polymerase. The reaction mixture is overlaid with mineral oil and subjected to 40 cycles of amplification. Each amplification cycle includes denaturation at 92° C. for 1 minute, annealing at 52° C. for 2 minutes and polynucleotide synthesis by primer extension (elongation) at 72° C. for 1.5 minutes. The amplified DNA homolog containing samples are then extracted twice with phenol/chloroform, once with chloroform, ethanol precipitated and are stored at −70° C. in 10 mM Tris-HCl, pH 7.5, and 1 mM EDTA.

Using 5' and 3' primers, efficient DNA homolog synthesis and amplification from the mRNA is achieved as shown by agarose gel electrophoresis. Following the above procedures, a gene library is constructed from the products of PCR amplifications. Equal portions of the products from different primer extension reactions may be mixed and the mixed product is used to generate a library of DNA homolog-containing vectors.

3. Linear DNA Expression Vectors

A DNA expression vector for use in a method of the invention for producing a library of DNA molecules is a linearized DNA molecule as described herein having two (upstream and downstream) cohesive termini adapted for ligation to a polypeptide gene.

A linear DNA expression vector is typically prepared by restriction endonuclease digestion of a circular or linear DNA expression vector of this invention to cut at two preselected restriction sites within the sequence of nucleotides of the vector adapted for ligation to produce a linear DNA molecule having the required cohesive termini that are adapted for ligation. A first terminus of the vector is complementary to both termini of the insert and to the second terminus of the vector.

A preferred DNA expression vector for use in a method of the invention for producing a library of DNA molecules is a linearized DNA molecule as described herein having two (upstream and downstream) cohesive termini adapted for ligation to a polypeptide gene.

A preferred linear DNA expression vector is typically prepared by restriction endonuclease digestion of a circular or linear DNA expression vector of this invention to cut at two preselected restriction sites within the sequence of nucleotides of the vector adapted for ligation to produce a linear DNA molecule having the required cohesive termini that are adapted for ligation.

4. Ligation Reactions to Produce Gene Libraries

To prepare an expression library of sequences, DNA homologs are prepared as described herein. The resulting PCR amplified products (2.5 µg/30 µl of 150 mM NaCl, 8 mM Tris-HCl, pH 7.5, 6 mM MgSO$_4$, 1 mM DTT, 200 µg/ml BSA) are digested at 37° C. with appropriate restriction enzymes such as those contained within the multiple cloning site of the lambda vectors of this invention. In cloning experiments which required a mixture of the products of the amplification reactions, equal volumes (50 µl, 1-10 µg concentration) of each reaction mixture are combined after amplification but before restriction digestion. The homologs are purified on a 1% agarose gel using the standard electroelution technique described in *Molecular Cloning A Laboratory Manual*, Maniatis et al., eds., Cold Spring Harbor, N.Y., 1982. After gel electrophoresis of the digested PCR amplified mRNA, the region of the gel containing DNA fragments of the desired base pairs are excised, electro-eluted into a dialysis membrane, ethanol precipitated and re-suspended in a TE solution containing 10 mM Tris-HCl, pH 7.5 and 1 mM EDTA to a final concentration of 50 ng/µl. The resulting DNA homologs represent a repertoire of polypeptide genes having cohesive termini adapted for directional ligation to the vector λfoo. These prepared DNA homologs are then directly inserted by directional ligation into linearized λfoo expression vector prepared as described below.

The λfoo expression DNA vector is prepared for inserting a DNA homolog by admixing 100 µg of this DNA to a solution containing 250 units each of appropriate restriction endonucleases and a buffer recommended by the manufacturer. This solution is maintained at 37° C. for 1.5 hours. The solution is heated at 65° C. for 15 minutes to inactivate the restriction endonucleases. The solution is chilled to 30° C. and 25 units of heat-killable (HK) phosphatase (Epicenter, Madison, Wis.) and CaCl$_2$ is admixed to it according to the manufacturer's specifications. This solution is maintained at 30° C. for 1 hour. The DNA is purified by extracting the solution with a mixture of phenol and chloroform followed by ethanol precipitation. The λfoo expression vector is now ready for ligation to the DNA homologs prepared as described herein. These prepared DNA homologs are then directly inserted into the restriction digested λfoo expression vector that prepared above by ligating 3 moles of DNA homolog inserts with each mole of the λfoo expression vector overnight at 5° C. Approximately 3.0×10$^5$ plague forming units are obtained after packaging the DNA with Gigapack® II Gold (Stratagene) of which >10% are recombinants. The ligation mixture containing the DNA homologs are packaged according to the manufacturers specifications using Gigapack® Gold II Packing Extract (Stratagene). The resulting λfoo expression libraries are then transformed into XL1-Blue cells.

In preparing a library of DNA molecules of this invention, a ligation admixture is prepared as described above, and the admixture is subjected to ligation conditions for a time period sufficient for the admixed collection of polypeptide genes to ligate (become operatively linked) to the plurality of DNA expression vectors to form the library.

Ligation conditions are conditions selected to favor a ligation reaction wherein a phosphodiester bond is formed between adjacent 3' hydroxyl and 5' phosporyl termini of DNA. The ligation reaction is preferably catalyzed by the enzyme T4 DNA ligase. Ligation conditions can vary in time, temperature, concentration of buffers, quantities of DNA molecules to be ligated, and amounts of ligase, as is well known. Preferred ligation conditions involve maintaining the ligation admixture at 4° C. to 25° C. for 1 to 24 hours in the presence of 1 to 10 units of T4 DNA ligase per milliliter (ml) and about 0.1 to 2 micrograms (µg) of DNA. Ligation buffer in a ligation admixture typically contains 0.5 M Tris-HCl (pH 7.4), 0.01 M MgCl$_2$, 0.01 M dithiothrietol, 1 mM spermidine, 1 mM ATP and 0.1 mg/ml bovine serum albumin (BSA). Other ligation buffers can also be used.

Exemplary ligation reactions are described in the Examples.

In a particularly preferred embodiment, the present invention contemplates methods for the preparation of a library of DNA molecules having one or more cistrons for expressing a fusion protein of this invention. In preferred embodiments, multiple cistrons are operatively linked at relative locations on the DNA molecule such that the cistrons are under the transcriptional control of a single promoter. Each multicistronic molecule is capable of expressing first, second, and optionally third polypeptides from first, second, and optional third overlapping cistrons, respectively, that can assemble to form, in a suitable host, a multimeric receptor on the surface of a lambdoid phage particle.

The method for producing a library of multicistronic DNA molecules comprises the steps of:
(a) Forming a ligation admixture by combining in a ligation buffer:
(i) polypeptide genes in the form of dsDNA, each having cohesive termini adapted for ligation, and
(ii) a plurality of DNA expression vectors in linear form, each having upstream and downstream first cohesive termini that are (a) adapted for receiving the polypeptide genes in a common reading frame, and (b) operatively linked to respective upstream translatable DNA sequences. The upstream translatable DNA sequence encodes a lambdoid phage matrix anchor protein and linker polypeptide, and translatable DNA sequences are operatively linked to respective upstream and downstream DNA expression control sequences.
(b) Subjecting the admixture to ligation conditions for a time period sufficient to operatively link the polypeptide genes to the vectors and produce a plurality of DNA molecules each having a first cistron for expressing the lambdoid phage matrix anchor polypeptide, a second cistron for expressing the fusion polypeptide, and an optional third cistron for expressing the monomeric polypeptide.

In preferred embodiments the lambdoid phage matrix anchor protein is a portion of the lambda pV tail protein. Also preferred is the use of a linker peptide that is derived from *C. fimi* endo-β-1,4-glucanase as described herein and contains sequences for the expression of the downstream inserted DNA sequences.

DNA expression vectors useful for practicing the above method are the expression vectors described in greater detail before.

In practicing the method of producing a library of multicistronic DNA molecules, it is preferred that the upstream and downstream first cohesive termini do not have the same nucleotide sequences as the upstream and downstream second cohesive termini. In this embodiment, the treating step (c) to linearize the circular DNA molecules typically involves the use of restriction endonucleases that are specific for producing said second termini, but do not cleave the circular DNA molecule at the sites that formed the first termini. Exemplary and preferred first and second termini are the termini defined by cleavage of λfoo with HindIII and Bam HI to form the upstream and downstream first termini. In this embodiment, other pairs of cohesive termini can be utilized at the respective pairs of first and second termini, so long as the termini are each distinct, non-complementary termini. Exemplary are the termini found on the vectors λV'sac, λV'mcs, λblue, and λfoo described herein.

Methods of treating the plurality of DNA molecules under DNA cleavage conditions to form linear DNA molecules with cohesive termini are generally well known and depend on the nucleotide sequence to be cleaved and the mechanism for cleavage. Preferred treatments involve admixing the DNA molecules with a restriction endonuclease specific for a endonuclease recognition site at the desired cleavage location in an amount sufficient for the restriction endonuclease to cleave the DNA molecule. Buffers, cleavage conditions, and substrate concentrations for restriction endonuclease cleavage are well known and depend on the particular enzyme utilized. Exemplary restriction enzyme cleavage conditions are described in the Examples.

5. Methods for Changing the Diversity of a Library

The present invention provides methods for changing the diversity of a library of lambdoid phage of this invention. These methods generally increase the diversity of the library, thereby increasing the pool of possible biologically active complexes from which to screen for a desired activity. Alternatively, the methods can be directed at enriching for a class of ligand-binding or substrate-binding complexes. The class is typically defined by the ability to bind a particular ligand or family of ligands, or the ability to bind a particular substrate or family of substrates.

a. Increasing Library Diversity by Mutation

A particularly preferred method for increasing diversity is to alter the amino acid residue sequence of one or more polypeptides of the ligand- or substrate-binding complex encoded by the genome of a phage of this invention. Alterations can be conveniently introduced at the nucleic acid level by mutation of the nucleic acid. The method can be practiced on a single species of nucleic acid coding a polypeptide of this invention, or can be practiced on a library of nucleic acids present in a library of phage of this invention.

Mutation of nucleic acid can be conducted by a variety of means, but is most conveniently conducted in a PCR reaction during a PCR process of the present invention. PCR mutagenesis can be random or directed to specific nucleotide sequences, as is generally well known. Conducting PCR under conditions favorable to random mutagenesis has been described previously, can involve the use of degenerate primers, by conditions of low stringency hybridization allowing mismatch such as by "error prone PCR". Similarly, directed mutagenesis involves the use of PCR primers designed to target a specific type of mutation into a specific region of nucleotide sequence.

In one embodiment, the invention contemplates increasing diversity of one or more ligand- or substrate-binding complexes by PCR-directed mutation of a domain present in a ligand- or substrate binding complex polypeptide of this invention.

Thus the invention contemplates a mutagenesis method for altering the specificity of a cloned gene present in a DNA vector of this invention. The method provides directed mutagenesis in a preselected domain of a gene which comprises subjecting a recombinant DNA molecule (rDNA) containing the cloned gene having a target domain to PCR conditions suitable for amplifying a preselected region of the domain. In the method, the rDNA molecule is subjected to PCR conditions that include a PCR primer oligonucleotide as described below constituting the first primer in a PCR primer pair as is well known to produce an amplified PCR product that is derived from the preselected domain but that includes the nucleotide sequences of the PCR primer. The second oligonucleotide in the PCR amplifying conditions can be any PCR primer derived from the gene to be mutagenized, as described herein.

Preferred are methods using an oligonucleotide of this invention as described below.

The length of the 3' and 5' terminal nucleotide sequences of a subject mutagenizing oligonucleotide can vary in length as is well known, so long as the length provides a stretch of nucleotides complementary to the target sequences as to hybridize thereto. In the case of the 3' terminal nucleotide sequence, it must be of sufficient length and complementarity to the target region located 3' to the region to be mutagenized as to hybridize and provide a 3' hydroxyl terminus for initiating a primer extension reaction. In the case of the 5' terminal nucleotide sequence, it must be of sufficient length and complementarity to the target region located 5' to the region to be mutagenized as to provide a means for hybridizing in a PCR overlap extension reaction as described above to assemble the complete polypeptide coding sequence.

Preferably, the length of the 3' and 5' terminal nucleotide sequences are each at least 6 nucleotides in length, and can be up to 50 or more nucleotides in length, although these lengths are unnecessary to assure accurate and reproducible hybridization. Preferred are lengths in the range of 12 to 30 nucleotides, and typically are about 18 nucleotides.

The nucleotide sequence located between the 3' and 5' termini adapted for mutagenizing a domain can be any nucleotide sequence, insofar as the novel sequence will be incorporated by the above methods. However, the present approach provides a means to produce a large population of mutagenized domains in a single PCR reaction by the use of a population of redundant sequences defining randomized or nearly randomized nucleotides in the region to be mutagenized.

Thus, the invention contemplates a method for increasing the diversity of a library of lambdoid phage particles comprising the steps of: a) providing a library of lambdoid phage particles according to the present invention, and b) mutating the ligand- or substrate-binding coding nucleotide sequence present in each DNA expression vector in the library to form a library of phage particles each containing a mutated nucleotide sequence.

The method of mutation can include manipulating the genomes of the phage particles in the library in order to isolate the nucleic acids in preparation for a mutagenizing PCR reaction. Manipulations of a phage library to isolate the phage genome for use in a PCR reaction is well known in the art.

In one embodiment, the method of mutation comprises subjecting the ligand- or substrate-binding coding nucleotide sequence to an error-prone polymerase chain reaction. In another embodiment, the method of mutation comprises subjecting the ligand- or substrate-binding coding nucleotide sequence to a method for mutating a region (domain) of the ligand- or substrate-binding coding nucleotide sequence using a region-directed oligonucleotide as described herein.

J. Method for Screening Proteins on the Surface of Lambda Phage Particles

Because the biologically active multimeric complex is linked to the phage in a surface accessible manner, the phage expressing the desired biologically active multimeric complex on its surface can be advantageously segregated from a population of phage by the use of a solid-phase substrate or ligand molecule. In preferred embodiments, the substrate or ligand molecule is linked, to a solid (aqueous insoluble) matrix such as agarose, cellulose, synthetic resins, polysaccharides and the like. For example, phage with the biologically active multimeric complex in a surface accessible manner can be segregated using immunoaffinity techniques such as panning of phage particles against a preselected substrate or ligand. In the panning method, substrate or ligand is applied to and retained in a microtiter dish and maintained under conditions that support retention of the substrate or ligand. An aqueous composition containing a population of phage, each expressing a biologically active multimeric complex in a surface accessible manner, is then contacted with the substrate or ligand under conditions that favor formation of a solid-phase substrate-enzyme or ligand-receptor complex. The dish is then washed to remove unbound phage, leaving the phage bound to the solid-phase substrate or ligand. The phage can then be removed and recovered by washing the dish with a buffer that promotes dissociation of the substrate-enzyme or ligand-receptor complex. Alternatively, the phage can be removed by digestion with a protease. Phage whose genome encodes the desired biologically active multimeric complex can thus be segregated from a population of phage.

The method of panning can be repeated by: 1) amplification of the removed phage particles by infection of a suitable host, 2) preparation of phage particles with biologically active multimeric complexes in a surface accessible manner, 3) immunoadsorption to a preselected substrate or ligand, and 4) removal of said immunoadsorbed phage particles. Thus, the method of panning to segregate the desired phage can be repeated multiple times to further enrich the population for phage particles with the desired biologically active multimeric complex.

Alternatively, a population of purified phage with a biologically active multimeric complex in a surface accessible manner can be admixed with a aqueous solution containing a preselected substrate or ligand. The substrate/enzyme or receptor/ligand binding reaction admixture thus formed is maintained for a time period and under binding conditions sufficient for a phage-linked enzyme-substrate or receptor-ligand complex to form. The phage-bound substrate (substrate-bearing) or ligand (ligand-bearing phage) are then separated and recovered from the unbound materials, such as by centrifugation, electrophoresis, precipitation, and the like.

A substrate or ligand analogue may be substituted for the substrate or ligand in the method of segregating a phage with the desired biologically active multimeric complex.

Phage expressing the desired biologically active multimeric complex on its surface can be advantageously segregated from a population of phage by the use of a solid-phase antibody molecule. In preferred embodiments, the antibody molecule is linked, to a solid (aqueous insoluble) matrix such as agarose, cellulose, synthetic resins, polysaccharides and the like. For example, phage with the biologically active multimeric complex in a surface accessible manner can be segregated using immunoaffinity techniques such as panning of phage particles against a preselected antibody immunoreactive with an epitope on the multimeric complex. In the panning method, antibody is applied to and retained in a microtiter dish and maintained under conditions that support retention of the antibody. An aqueous composition containing a population of phage, each expressing a biologically active multimeric complex in a surface accessible manner, is then contacted with the antibody under conditions that favor formation of a solid-phase multimeric complex-antibody complex. The dish is then washed to remove unbound phage, leaving the phage bound to the solid-phase antibody. The phage can then be removed and recovered by washing the dish with a buffer that promotes dissociation of the multimeric complex-antibody complex. Alternatively, the phage can be removed by digestion with a protease. Phage whose genome encodes the desired biologically active multimeric complex can thus be segregated from a population of phage. This process can be repeated to enrich the phage population for the desired activity as described herein for the panning method.

Phage expressing a desired catalytically active multimeric complex can be identified in a population of phage by catalysis of a preselected substrate. In preferred embodiments, the substrate molecule is contacted with the phage particle and maintained under conditions that support catalysis of the substrate to form a detectable product or products. Phage whose genome encodes a desired catalytically active multimeric complex can thus be identified in a population of phage particles.

K. Diagnostic Methods and Systems

The present invention contemplates various assay methods that would utilize the biological activity of the fusion protein of the present invention, for example to detect the presence, and preferably amount, of a preselected receptor, ligand, enzyme or substrate (i.e., target material) with which the fusion protein binds or reacts. The assay can be conducted on a sample such as a biological fluid or tissue sample using a fusion protein or phage displaying a fusion protein of this invention as an reagent to form an product whose amount relates, either directly or indirectly, to the amount of material (target material) to be detected or measured in the sample.

Those skilled in the art will understand that there are numerous well known clinical diagnostic chemistry procedures in which a reagent of this invention can be used to form an reaction product whose amount relates to the amount of target material present in a body sample. Thus, while exemplary assay methods are described herein, the invention is not so limited.

Various heterogenous and homogeneous protocols, either competitive or noncompetitive, can be employed in performing an assay method of this invention. Examples of types of assays which can utilize a fusion protein of the invention include competitive and non-competitive binding assays in either a direct or indirect format. Examples of such assays are the ELISA assays, binding assays, radioimmunoassay (RIA), the sandwich (immunometric) assay, and the like. Detection of a target material using the fusion protein of the invention can be done utilizing assays which are run in either the forward, reverse, or simultaneous modes, including histochemical assays on physiological samples. Those of skill in the art will know, or can readily discern, other assay formats without undue experimentation.

In addition, solid or liquid phase enzyme assays, are contemplated in which the fusion protein has catalytic activity that are useful for detecting the presence of substrate by generation of product.

The fusion protein of the invention can be bound to many different carriers and used to detect the presence of a target material. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding fusion protein, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bio-luminescent compounds. Those of ordinary skill in the art will know of other suitable labels for binding to the monoclonal antibodies of the invention, or will be able to ascertain such, using routine experimentation. Furthermore, the binding of these labels to the fusion protein or phage particle of the invention can be done using standard techniques common to those of ordinary skill in the art.

For purposes of the invention, a target material may be detected by the fusion protein of the invention when present in samples of biological fluids and tissues. Any sample containing a detectable amount of target material can be used. A sample can be a liquid such as a natural or man-made source, industrial or biological waste or by product, urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the fusion protein to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

A further diagnostic method utilizes the multivalency of a lambdoid phage particle to cross-link ligand, thereby forming an aggregation of multiple ligands and phage particles, producing a precipitable aggregate. This embodiment is comparable to the well known methods of immune precipitation. This embodiment comprises the steps of admixing a sample with a plurality of phage particles of this invention to form a binding admixture under binding conditions, followed by a separation step to isolate the formed binding complexes. Typically, isolation is accomplished by centrifugation or filtration to remove the aggregate from the admixture. The presence of binding complexes indicates the presence of the preselected ligand to be detected.

Thus, in a preferred embodiment, a method for detecting the presence of a preselected target in a sample comprises the steps of:

a) admixing a sample containing a preselected target with a recombinant lambdoid bacteriophage of this invention, wherein the preselected polypeptide defines a biologically active ligand or receptor able to bind the preselected target, under binding conditions sufficient for the target-binding bacteriophage to bind the target and form a target-ligand or receptor complex;

b) detecting the presence of the complex, and thereby the presence of the preselected target.

The binding conditions can vary widely depending upon the type of binding activity of the fusion protein, which in turn depends on the type of binding ligand, as is well appreciated in the art. Because the invention is not directed to the particular type of biological activity being displayed, it is to be appreciated that the binding conditions are not to be so limited based on a particular ligand.

The detection of the complex or bound target can be accomplished by a variety of means as discussed earlier. However, in one preferred embodiment the detecting step can comprise detecting the presence of the bacteriophage particles, such as with an antibody specific for a phage antigen, and thereby detect the presence of the preselected target.

The present invention also describes a diagnostic system, preferably in kit form, for assaying for the presence of a preselected substrate in a sample where it is desirable to detect the presence, and preferably the amount, of the substrate in a sample according to the diagnostic methods described herein. Alternatively, the present invention also describes a diagnostic system, preferably in kit form, for assaying for the presence of a preselected ligand, or antigen, in a sample where it is desirable to detect the presence, and preferably the amount, of the ligand or antigen in a sample according to the diagnostic methods described herein.

In another embodiment, a diagnostic system is contemplated for assaying for the presence of an enzyme or receptor in a body fluid sample such as for monitoring the fate of therapeutically administered enzyme or receptor. The system includes, in an amount sufficient for at least one assay, an enzyme or receptor as a control reagent, and preferably a preselected amount of substrate or ligand, each as separately packaged immunochemical reagents.

The sample can be a tissue, tissue extract, fluid sample or body fluid sample, such as blood, plasma or serum.

The diagnostic system includes, in an amount sufficient to perform at least one assay, a lambdoid phage or substrate- or ligand-binding multimeric receptor according to the present invention, as a separately packaged reagent.

Exemplary diagnostic systems for detecting a preselected substrate or ligand in the solid phase and utilizing a lambdoid phage of this invention are described in the Examples.

In embodiments for detecting substrate or ligand in a body fluid, a diagnostic system of the present invention can include a label or indicating means capable of signaling the formation of an substrate- or ligand-binding complex containing a bacteriophage displaying an enzyme or ligand of the present invention.

Phage of this invention can be labeled when used in a diagnostic method of this invention. Preferred labels include radioactively labeled nucleic acids incorporated into the phage genome, or radioactively labeled amino acids incorporated into protein components of the phage particle. Preparation of labeled phage can be routinely prepared by growing phage as described herein, but including radiolabeled nucleotides or radiolabeled amino acids in the culture medium for incorporation into nucleic acids or polypeptides of the phage, respectively. Exemplary labels are $^3$H-thymidine or $^{35}$S-methionine. Other isotopic labels and other nucleotide or amino acid precursors are readily available to one skilled in the art. The labeled phage preferably contains sufficient label to be detectable in a ligand-binding assay of this invention, i.e., the phage is detectably labeled.

As used herein, the term "package" refers to a solid matrix or material such as glass, plastic (e.g., polyethylene, polypropylene or polycarbonate), paper, foil and the like capable of holding within fixed limits a multimeric receptor, lambdoid phage or library of phage of the present invention. Thus, for example, a package can be a glass vial used to contain milligram quantities of a labeled phage preparation, or it can be a microtiter plate well to which microgram quantities of a contemplated receptor, ligand, antibody or phage particle(s) have been operatively affixed, i.e., linked so as to be capable of binding a substrate or ligand.

A diagnostic system of the present invention preferably also includes a label or indicating means capable of signaling the formation of a binding reaction complex containing a substrate- or ligand-binding multimeric receptor or phage complexed with the preselected substrate or ligand.

The word "complex" as used herein refers to the product of a specific binding reaction such as an phage-substrate or receptor-substrate reaction. Alternatively, the word "complex" as used herein refers to the product of a specific binding reaction such as an phage-ligand or receptor-ligand reaction. Exemplary complexes are substrate-enzyme or receptor-ligand products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed polypeptide, or phage particle that is used in a diagnostic method. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189-231, 1982, which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a substrate-enzyme or receptor-ligand complex has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$indium of $^3$H.

The linking of labels, i.e., labeling of, polypeptides and proteins is well known in the art. For instance, proteins or phage can be labeled by metabolic incorporation of radioisotope-containing amino acids provided as a component in the culture medium. See, for example, Galfre et al., *Meth. Enzymol.*, 73:3-46, 1981. The techniques of protein conjugation or coupling through activated functional groups are particularly applicable. See, for example, Aurameas, et al., *Scand. J. Immunol.*, Vol. 8 Suppl. 7:7-23, 1978, Rodwell et al., *Biotech.*, 3:889-894, 1984, and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or phage of the present invention. Exemplary specific binding agents are antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of a preselected substrate or ligand in a fluid sample. "ELISA" refers to an enzyme-linked immunosorbent assay that employs an antibody or antigen bound to a solid phase and an enzyme-antigen or enzyme-antibody conjugate to detect and quantify the amount of an antigen present in a sample and is readily applicable to the present methods. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; No. 3,850,752; and No. 4,016,043, which are all incorporated herein by reference.

Thus, in some embodiments, a phage or fusion polypeptide of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides can be used that are well known to those skilled in the art. Exemplary adsorption methods are described herein.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

Instructions for the use of the packaged reagent(s) are also typically included. "Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

The packaging materials discussed herein in relation to diagnostic systems are those customarily utilized in diagnostic systems.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise an enzyme or receptor of the invention which is, or can be, detectably labelled. The kit may also have containers containing any of the other above-recited immunochemical reagents used to practice the diagnostic methods.

EXAMPLES

The following examples are intended to illustrate, but not limit, the scope of the invention.

1. Construction of a Tricistronic Expression Vector λfoo for Displaying a Protein on the Surface of Lambda Phage Particles Expression libraries in bacteriophage M13 have previously been constructed for generating a large number of Fab antibody fragments displayed on the surface of filamentous phage. The displayed Fabs can be screened directly for a desired binding activity. These systems are primarily useful in the surface display of secreted proteins and do not contain design features that provide for the surface display of nonsecreted or cytoplasmic proteins. While these systems provide for the expression of multimeric proteins, two separate cloning steps are required. In addition, these systems do not provide for the expression of multimeric proteins consisting of both the surface display fusion protein and the unfused wild-type protein monomer or monomers. Such expression may be required for the proper assembly of multimeric proteins. The assembly of the displayed protein into multimers may be required for the recognition of the multimeric complex by immunological reagents such as antibodies and for biological activities such as catalytic, substrate- or ligand-binding activities.

The main criterion used in choosing a vector system was the necessity of generating a system which would be more appropriate for proteins that fold in the cytoplasm. Bacteriophage lambda was selected as the expression vector for several reasons. First, in vitro packaging of phage DNA was the most efficient method of reintroducing DNA into host cells. Second, it was possible to detect protein expression at the level of a single plaque. Finally, bacteriophage lambda is assembled in the cytoplasm from proteins which are produced in the cytoplasm.

A lambda phage expression system, λfoo, which produces biologically active proteins displayed on the surface of the phage particle was constructed. The biologically active proteins described in this invention are multimeric proteins. The biologically active protein consists of a truncated pV and a monomer of the displayed protein which are linked during translation by a peptide bond to form a fusion protein and one or more free monomers. The fusion protein and one or more free monomers assemble to form a multimeric complex.

The fusion protein and monomers are encoded by genes inserted into the λ vector and are expressed by conditional suppression. Conditional suppression allows the expression of the truncated pV' protein, fusion protein, and monomeric proteins from a single mRNA transcript. The expression of three separate proteins from a single mRNA transcript in the λfoo expression vector is termed tricistronic expression and is described further herein. In addition, conditional suppression expresses the fusion protein and monomers in a ratio relative to the other λ proteins which favors the assembly of functional phage particles.

One of the biologically active proteins of this invention comprises a truncated pV and β-gal fusion protein (pV-β-gal fusion protein) and β-gal monomers which are also assembled to form a tetrameric complex. These proteins are encoded by genes inserted into the λβ-gal vector and are expressed by conditional suppression. A tetrameric complex comprising the pV-β-gal fusion protein and the individual β-gal monomers must be formed for biological activity. Three monomers of β-gal assemble with the pV-β-gal fusion protein to form the biologically active β-gal protein on the surface of the phage particles. The biological activity of β-gal refers to the ability of β-gal to cleave a galactoside sugar to form two sugars.

Similarly, a truncated pV and BPA fusion protein (pV-BPA fusion protein) and BPA monomers also assembled to form a tetrameric complex. These proteins are encoded by genes inserted into the λBPA vector and are expressed by conditional suppression. A tetrameric complex comprising the pV-BPA fusion protein and the individual BPA monomers must be formed for biological activity. Three monomers of BPA assemble with the pV-BPA fusion protein to form the biologically active BPA protein on the surface of the phage particles. The biological activity of BPA refers to the ability of BPA to bind mucin.

One of skill in the art would realize that the truncated pV protein may be fused with a biologically active protein, a monomer which assembles with identical monomers to form a homomeric biologically active protein, or a monomer which assembles with nonidentical monomers to form a heteromeric biologically active protein.

A series of λ phage vectors with pV', a truncated form of pV, were constructed and are described herein.

a. Construction of the Expression Vector λV'sac

The first vector, λV'sac was constructed with a truncated pV protein to determine if functional phage particles would be assembled with the truncated pV protein. Wild-type pV is a 25.8 kDa protein and contains 246 amino acid residues. λV'sac has an amber stop codon, TAG, in place of GAG coding for Glu at amino acid residue 177 of the pV gene and produces a truncated pV protein which is 18.8 kDa with only 176 amino acid residues when the pV protein is expressed in a nonsuppressor strain. The truncated pV, designated pV', is therefore 70 amino acids shorter than the wild-type pV. pV' is expressed in all of the λ vectors described in this invention. λV'sac also has a unique SacI restriction site, two base pairs downstream of the amber codon, which was used as an insertion site in the construction of additional λ vectors (FIG. 1).

1) Preparation of λV'sac

λV'sac was generated from a combination of the left arm of λ1685 [bI007Δ(att-int) ΔssIIλ1-2 KH54 srIλ4°nin5 shndIIIλ6°] and the right arm of λ2000 (a derivative of λ2001 lacking the polylinker sites (Karn et al., $Gene$, 32:217, 1984; λ2001 is available from the American Type Culture Collection, ATCC No. 37474). λV'sac contains an amber mutation and a unique SacI restriction site in the V gene of λ phage.

Figure 1:
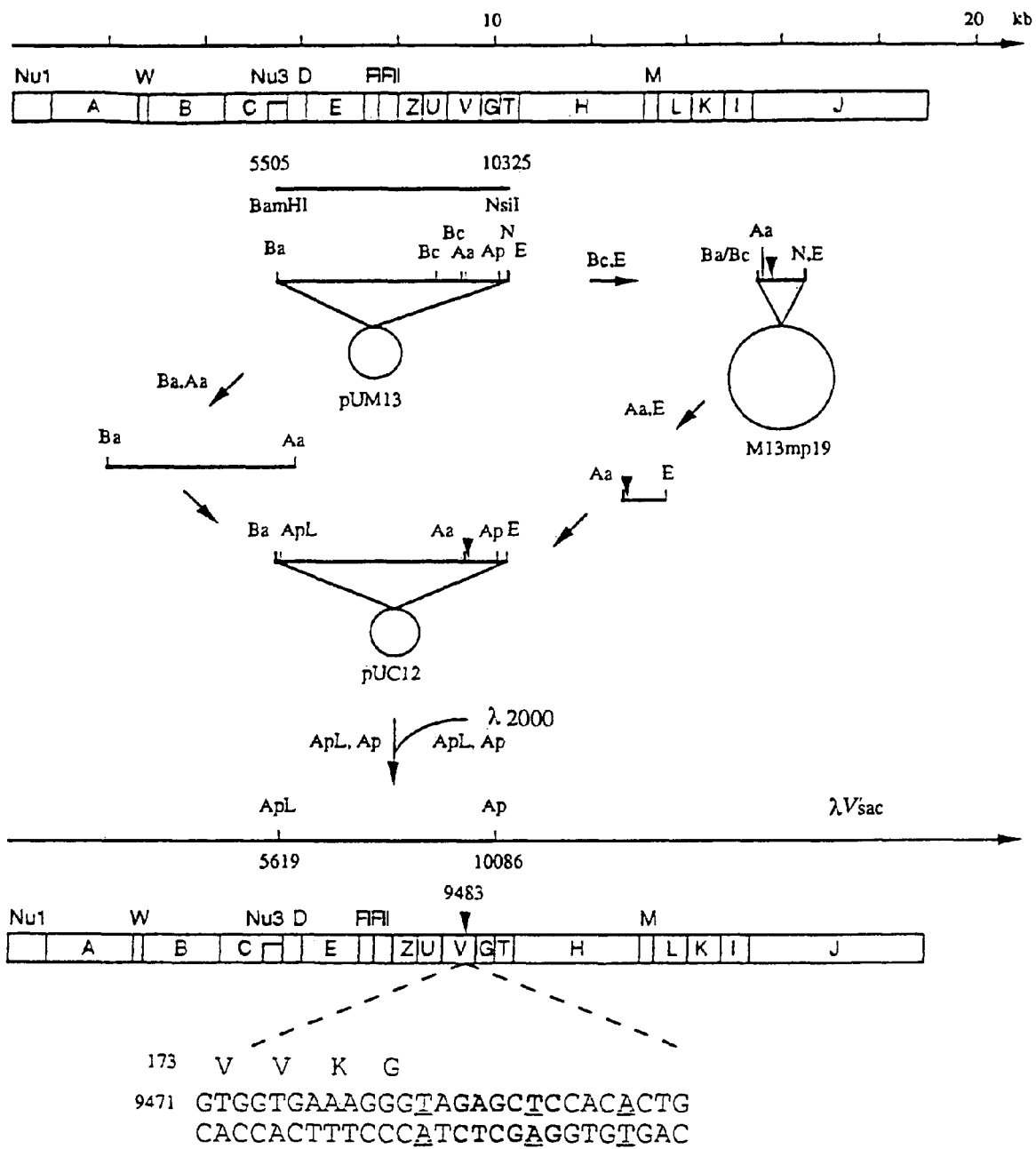
FIG. 1 illustrates a flow chart of the construction of the λV' sac vector. Also indicated is the partial nucleotide and amino acid sequence of the λV' sac vector. The amino acid sequence is given in SEQ ID NO 9. The top strand of the nucleotide sequence from left to right is given in SEQ ID NO 10. The bottom strand of the nucleotide sequence from left to right is given in SEQ ID NO 11. The left arm of λ phage is depicted with genes Nu1 through J shown as boxes. The arrow at the top of the figure indicates the number of kilobase pairs (kb) of the λ vector. The DNA segment from nucleotide 5505 to 10,325 and encoding genes Nu3 through G was removed from the λ vector by digestion with the enzymes BamHI and NsiI. This fragment is shown as a line with nucleotide numbers below the topmost λ genetic map. Insertion of the DNA fragment into the M13 mp19 and pUC12 vectors, site-directed mutagenesis to introduce the amber stop codon and Sac I restriction site, and subsequent combination with the λ2000 vector to create the λV' sac vector are as described in Example 1a1. A portion of the resulting λV' sac vector is shown at the bottom of the figure consisting of the amino acid and nucleotide sequence of part of the mutagenized V gene. The nucleotide positions which were mutagenized are underlined and a newly created Sac I site is indicated in boldface type. The amber suppressor stop codon is indicated by the nucleotide sequence TAG which is underlined. Numbers at the left side from top to bottom indicate the amino acid number of the pV gene and the nucleotide sequence from the left arm of λ, respectively. Abbreviations used to indicate the corresponding restriction sites are: Ba, BamHI; Bc, BclI; Aa, AatII; Ap, ApaI; N, NsiI; E, Ecori: and ApL, ApaLI.

To generate λV'sac, λ1685 was digested with BamHI and NsiI to release a 4.82 kb BamHI-NsiI segment of DNA which contained genes Nu3 through G (FIG. 1). The 4.82 kb BamHI-NsiI segment of DNA was inserted into pUM13 (Maruyama et al., $Gene$, 120:135-141, 1992) which was also digested with BamHI and NsiI using T4 DNA ligase and standard protocols such as those described in $Current Protocols in Molecular Biology$, Ausubel et al., eds., John Wiley and Sons, NY, 1987. The pMU13 plasmid is a derivative of pBluescribe M13$^+$ (Stratagene, La Jolla, Calif.) and was made by inserting an oligonucleotide which contained additional XhoI and NsiI restriction sites in frame into the polylinker sequence. A 0.96 kb BclI-EcoRI fragment from the pUM13 plasmid containing the segment of λ1685 was inserted into the BamHI and EcoRI site of the M13 mp19 phage vector (Pharmacia, Piscataway, N.J.). Site-directed mutagenesis was performed as described in Zoller et al., $DNA$, 3:479, 1984 using the single-stranded form of phage DNA as template and the oligonucleotide 5'-AGTGTG-GAGCTCTACCCTTTC-3' (SEQ ID NO 2). The site-directed mutagenesis introduced an amber codon and a SacI site following nucleotide 9482 at amino acid 176 of the V gene. The segment containing the amber codon and SacI site was excised by digesting the M13 mp19 construct with AatII and EcoRI. This fragment and a 4.9 kb BamHI-AatII fragment of the pUM13 clone were ligated at the common AatII site and then into the pUC12 vector (Karn, et al., $Gene$, 32:217, 1984) which was digested with BamHI and EcoRI. A 4.5 kb fragment was excised by digestion with ApaLI and ApaI from this construct and ligated with a 5.6 kb left arm of λ1685 digested with ApaLI and a 33 kb right arm of λ2000 digested with ApaI. This final ligation produced the λV'sac vector which contains an amber mutation and a SacI restriction site in the V gene, the left arm of λ1685, and the right arm of λ2000.

2) Expression of pV' and Wild-Type pV Proteins from λV'sac by Conditional Suppression Conditional suppression was used to characterize the expression of pV' and wild-type pV encoded by λV'sac with several $E. coli$ strains. This characterization was performed to verify that functional phage particles could be produced by with only the truncated pV protein. Conditional suppression was used to vary the amount of pV' and wild-type pV expressed by varying the amber suppressor $E. coli$ strain used to express the pV proteins. The $E. coli$ strains were Q1 (thr, leu, lac, supE), EQ170 [Δ(lac-proAB), nalA, rif, argE$_{am}$, metB, supE], EQ166 [Δ(lac-proAB), nalA, rif, argE$_{am}$, ara], CA168 (Hfr C, lacIO2, gal, supB), MC8 (lac125, suDG, trp$_{am}$), TG1 [Δ(lac-proAB), supE, thi, hsdD5/F', traD36, proAB$^+$, lacI$^q$ZΔM15], EQ82 (hsdR, supE, supF, met), and Q358 (hsdR, supE, Ø80$^R$). EQ166 does not produce a suppressor tRNA which can suppress an amber mutation and is therefore designated as an su$^-$ strain. The remaining hosts contain a suppressor tRNA which can suppress the amber mutation and are therefore designated su$^+$.

The su$^+$ strains tested in this invention produce varying amounts of suppressor tRNA. The frequency with which the suppressor tRNA inserts an amino acid residue at the amber codon is dependent upon the amount of suppressor tRNA present in the $E. coli$ strain. Therefore, the frequency with which the su$^+$ strains tested in this invention would insert an amino acid residue at the amber codon would vary and thus the ratio of truncated pV to wild-type pV produced would vary.

Growth of pV'sac in several $E. coli$ strains was characterized to verify that functional phage particles would be formed when only the truncated pV protein was incorporated into the tail portion of the phage particle. The phage particles produced in the $E. coli$ strains with a suppressor tRNA contain a wild-type pV in addition to the truncated pV due to read-through and suppression of the amber mutation by the host, respectively. The full-length or wild-type pV is produced by the insertion of a codon at the amber codon by the suppressor tRNA. The phage particles produced in the $E. coli$ strains without a suppressor tRNA contain only the truncated pV due to lack of suppression of the amber mutation by the host. The formation of plaques in the $E. coli$ host EQ166 (su$^-$) would therefore confirm previous findings that a pV molecule that is truncated at the carboxy terminus can participate in functional phage particle assembly.

Growth in the $E. coli$ strains was determined by the formation of plaques on a lawn on $E. coli$. Briefly, to form plaques on a lawn of $E. coli$, phage particles are mixed with the $E. coli$ cells and incubated at 37° C. for 15 minutes to allow the phage to adsorb to the lamB receptor on the surface of the cells and inject the λ DNA into the cells. Cells and phage are then mixed with 0.7% (w/v) agar in a suitable medium which has been melted and equilibrated to 48° C. After mixing, the mixture is poured onto the surface of 2% (w/v) agar in a suitable medium, allowed to solidify, and incubated at 37° C.

until the *E. coli* has grown to form a confluent layer, or lawn, on the surface of the agar. The presence of clear areas on the lawn represent where a functional phage particle has infected the *E. coli* cells and caused lysis of the *E. coli* cells. Thus, a plaque represents a functional phage particle. Because pV protein is required for the assembly of a functional phage particle, a plaque also represents that pV protein capable of assembly to form a functional phage particle was expressed from the λ vector which encodes the pV protein. The morphology of the plaque, such as size and clarity, is an indication of the number of functional phage particles produced by the *E. coli* strain.

λV'sac produced plaques which were similar in size as one of the parental vectors, λ2001, on many of the *E. coli* strains tested. This indicates that the truncated pV expressed from λV'sac produced functional phage particles as well as λ2001 with wild-type pV in the nonsuppressor *E. coli* strains tested.

b. Construction of Expression Vector λV'mcs

λV'mcs was constructed from λV'sac by inserting double-stranded synthetic oligonucleotides which contain multiple restriction sites at the unique SacI site of λV'sac to form a multiple cloning site (mcs). The restriction sites inserted were SacI, HindIII, BamHI, SmaI, SalT, and EcoRI as shown in FIG. 2 where the resultant MCS amino acid sequence (SEQ ID NO 12) and encoding nucleotide sequence (SEQ ID NO 13) are shown.

1) Expression of pV Proteins from λV'mcs by Conditional Suppression

Growth of the λV'mcs was characterized with several *E. coli* hosts. λV'mcs grows well on su⁻ hosts such as EQ166 but produces a slightly smaller plaque on su⁺ hosts such as Q358. λV'mcs produces a truncated pV' protein on su⁻ hosts and a combination of pV' and a pV' protein with the amino acid residues encoded by the mcs inserted at amino acid residue 176 of the pV protein in su⁺ hosts. Thus, the presence of the amino acid residues encoded by the mcs in the pV protein may effect the assembly of infectious phage particles in su⁺ hosts.

c. Construction of Expression Vector λblue-α

λblue-α was constructed from λV'sac and λV'mcs by inserting a unique NotI site and the multiple cloning site from pUC19 (Pharmacia, Piscataway, N.J.) at the unique SacI site. In addition, the α-peptide sequence of the β-gal gene with the β-gal ribosome binding site or Pribnow box and an SfiI site were inserted downstream of the multiple cloning site. Thus, λblue-α is unique from the previously constructed λ vectors by the presence of the multiple cloning site from pUC19, a unique NotI site, and the α-peptide of the β-gal gene.

The α-peptide of the β-gal gene provides α-complementation of the β-gal gene to produce functional β-gal in an appropriate *E. coli* host and is used in the identification of λ vectors containing a DNA insert. If a DNA insert is ligated into the mcs between the β-gal promoter and the α-peptide, the α-peptide will not be expressed and α-complementation of the β-gal gene to produce functional β-gal will not occur. Functional β-gal activity is detected by the formation of a blue color by cleavage of the β-gal substrate 5-bromo-4-chloro-3-indoyl-β-D-galactopyranoside (X-gal). When a DNA insert is not present, α-complementation occurs, functional β-gal is produced, and X-gal is cleaved to form a blue color. When X-gal is included in the medium, phage plaques formed by a λ vector with an insert in the mcs will remain colorless and phage plaques formed by a λ vector without an insert in the mcs will turn blue. Thus, the presence of the α-peptide in λblue-α provides a means for the identification of recombinants containing a DNA insert in the mcs.

The first step in the construction of λblue-α was to digest pUC19 with HindIII and NarI to generate a fragment which contains the multiple cloning site of pUC19 and the α-peptide sequence of the β-gal gene. This fragment was ligated with an oligonucleotide linker containing a NotI site (SEQ ID NOs 3 and 4) and NarI and SacI compatible overhangs on the 5' and 3' ends, respectively. The two oligonucleotides given in SEQ ID NOs 3 and 4 were annealed to generate the oligonucleotide linker. The ligated fragment consisting of the α-peptide sequence of the β-gal gene, the multiple cloning site of pUC19, and the oligonucleotide linker containing a NotI site were then ligated with the left and right vector arms from λV'mcs and λV'sac, respectively. The ligated fragment was ligated with the left arm of λV'mcs digested with HindIII and the right arm from λV'sac digested with SacI.

1) Expression of pV' and Wild-Type pV Proteins from λblue-α by Conditional Suppression Conditional suppression was used to characterize growth of λblue-α in several *E. coli* strains. The ability of λblue-α without an insert to express the α-peptide of β-gal and thus provide the α-complementation needed to produce functional β-gal was determined by forming plaques on a lawn of *E. coli* as described above and with the substrate X-gal in the medium. Plaques formed by λblue-α formed blue color in the presence of X-gal indicating that λblue-α did not contain a DNA insert and expressed the α-peptide. The λblue-α grew well on all *E. coli* hosts tested indicating that the construction of the vector did not interfere with expression of genes downstream of the V gene.

d. Construction of Expression Vector λblue

λblue was constructed from λblue-α by inserting a double-stranded synthetic oligonucleotide which encodes a unique restriction site, SfiI, a ribosomal binding site, and an initiator methionine codon following the amber stop codon in pV and before the mcs. The insertion of this oligonucleotide removed the original SacI site adjacent to the amber stop codon.

1) Expression of pV' and Wild-Type pV Proteins from λblue by Conditional Suppression Conditional suppression was used to characterize expression of λblue by conditional suppression in several suppressor and nonsuppressor *E. coli* strains. λblue produced smaller phage plaques than λV'sac and λV'mcs when plated with EQ166 (su⁺) and Q358 (su⁻).

e. Construction of Expression Vector λfoo

λfoo was constructed by inserting a double-stranded synthetic oligonucleotide encoding a linker peptide consisting of alternating prolyl and theonyl residues, termed the Pro-Thr sequence of *Cellulomonas fimi* endo-β-1,4-glucanase (Wong, et al., *Gene,* 44:315-324, 1986), at the unique SfiI site of λblue (FIG. 2). In the endo-β-1,4-glucanase molecule the Pro-Thr box links two domains, the cellulose-binding domain and catalytic domain in *C. fimi* oxoglucanase (Cex) and endoglucanase (CenA), and is similar in structure to the hinge-region of IgA1 immunoglobulins (Ong et al., *Biotechnology,* 7:604-607, 1989). The Pro-Thr linker in λfoo serves to separate pV' from the fused foreign protein and may prevent the two domains from interfering with each other during folding and assembly of the phage tail proteins to form the phage tail matrix. The linker also allows foreign proteins to be cleaved from the phage particles by digestion with enzymes such as *C. fimi* protease (Gilkes et al., *J. Biol. Chem.,* 263:10401-10407, 1988) or collagenase.

The Pro-Thr linker sequence also provides the 5' expression control elements required to express a DNA sequence inserted in the mcs of λfoo (FIG. 2). Within the Pro-Thr linker sequence are a ribosome binding site and methionine start codon upstream of the HindIII, BamHI, SacI, and EcoRI cloning sites. Thus, a DNA sequence inserted into any of these sites that is in the same reading frame as the start codon methionine would be expressed from the ribosome binding site and start codon contained within the Pro-Thr linker sequence. Expression from this ribosome binding site and start codon is not dependent on the presence of a suppressor tRNA and thus occurs in both su⁻ and su⁺ hosts to produce a monomer of the protein encoded by the inserted DNA.

1) Expression of pV' and Wild-Type pV Proteins from λfoo by Conditional Suppression Conditional suppression was used to characterize expression of λfoo by conditional suppression in several *E. coli* strains. λfoo produced smaller plaques than λV'sac and λV'mcs when plated with EQ166 (su⁺) and Q358 (su⁻).

2. Methods of Producing a Functionally Active β-gal Fusion Protein on the Surface of Lambda Phage Particles To express *E. coli* β-gal fused to the carboxy terminus of pV and incorporate β-gal into the surface of phage particles, the entire β-gal gene was inserted into and expressed by the λfoo vector.

a. Construction of a Tricistronic Expression Vector λβ-gal for Producing a Biologically Active Multimeric Protein on the Surface of Lambda Phage Particles The tricistronic expression vector λβ-gal was constructed by ligating the β-gal gene excised from pMC1871 (Pharmacia, Piscataway, N.J.) to the left arm of λfoo and the right arm of λV'mcs. The left arm of λfoo was used because it contains the Pro-Thr linker sequence between the V gene, amber codon, and SfiI site. The right arm of λV'mcs was used because it does not contain the α-peptide of the β-gal gene that provides a means for α-complementation. If the right arm of a vector, such as λfoo, which contains the α-peptide of the β-gal gene were used in the construction of the λβ-gal vector, both the vector without insert and the β-gal vector would have β-gal activity and generate plaques with a blue color in the presence of X-gal. Thus, it would not be possible to distinguish between phage containing the β-gal insert and those without the β-gal insert by the color screening method described herein.

1) Insertion of β-gal Gene into λV'mcs

The β-gal gene was inserted into the BamHI site of λfoo to generate λβ-gal. This was performed by first digesting pMC1871 containing the β-gal gene, λfoo, and λV'mcs with BamHI and then ligating the fragments together with T4 DNA ligase.

2) Expression of pV/β-gal Fusion Protein and Incorporation into Phage Particles by Conditional Suppression The expression of recombinant phage containing the left arm of λfoo, the β-gal insert, and the right arm of λV'mcs was characterized by conditional suppression in several *E. coli* strains. Growth in a su⁻ host would express only the pV' protein and the β-gal monomeric protein. The pV'-β-gal fusion protein consisting of the pV', linker peptide, and β-gal monomer would not be expressed. The fusion protein would not be expressed because a tRNA which can insert an amino acid at the amber codon in the pV coding sequence is not present in a su⁻ host. The pV protein would therefore be truncated at the amber codon present at amino acid residue 177 of the pV protein. The monomeric β-gal protein would be expressed from the ribosome binding site and methionine start codon contained within the coding sequence of the Pro-Thr linker. The monomeric β-gal protein is encoded by the DNA insert in the λ vector. Thus, although the β-gal monomers expressed from the ribosome binding site in the Pro-Thr linker peptide would assemble to form a β-gal multimeric complex with enzymatic activity, the β-gal multimeric complex would not be incorporated into phage particles by means of the pV-β-gal fusion protein.

Growth in a su⁺ host would express the pV', pV-β-gal fusion protein, and β-gal monomeric proteins from the tricistronic message. The pV-β-gal fusion protein, consisting of pV', the Pro-Thr linker peptide, and monomeric β-gal would be incorporated into the phage particle by means of the pV' matrix anchor. Monomeric β-gal expressed from the ribosome binding site and start codon in the Pro-Thr linker sequence would also be expressed and assemble with the pV-β-gal fusion protein to form a enzymatically active β-gal on the surface of the phage particles.

The recombinant phage, β-gal, grown on *E. coli* host EQ166 formed blue plaques on agar plate containing the color indicator X-gal, indicating that active β-gal had been produced. However, only β-gal monomers were produced in this su⁻ strain and β-gal was not incorporated onto the surface of the phage particles. Translation of the wild-type β-gal monomers was initiated at the ribosomal binding site in the linker peptide of the construct.

The recombinants were then grown on host strains with varying amounts of suppressor activity to determine whether functional phage particles were produced. The phage grew well and thus produced high numbers of phage particles in a liquid medium with EQ166 (su⁻), CA168 ($su_B^+$) and MC8 ($su_\gamma^+$). However, the phage grew poorly on strains which produce higher numbers of suppressor tRNAs such as TG1 ($su_{II}^+$), Q1 ($su_{II}^+$), EQ170 ($su_6^+$), and EQ82 ($su_{II}^+su_{III}^+$). On a solid medium, λβ-gal made smaller plaques on TG1 (su⁺) and Q358 ($su_{II}^+$) than when grown in EQ166 (su⁻) and MC8 (su⁺). These results suggest that the production of large amounts of fusion protein (pV'-β-gal) by hosts which produce higher numbers of suppressor tRNAs have an adverse effect on phage particle assembly. The frequency with which an amino acid residue is inserted at the amber codon determines the ratio of pV'-β-gal fusion protein, pV' protein, and β-gal protein produced in the strain. If an amino acid residue is inserted at the amber codon, a pV'-β-gal fusion protein, pV' protein, and β-gal monomeric protein are produced. If an amino acid residue is not inserted at the amber codon, the pV' and β-gal proteins are produced. The pV' protein is produced by initiation of translation at the naturally-occurring methionine at the start of the coding sequence. The pV' protein is terminated at amino acid residue number 176 at the position of the amber codon in the absence of a suppressor tRNA. The β-gal monomer is produced by initiation of translation at the methionine which is encoded by the Pro-Thr linker sequence between the nucleotide sequence encoding the pV' protein and the inserted DNA encoding β-gal. Therefore, the *E. coli* strains tested in this invention produce varying ratios of the pV'-β-gal fusion protein, pV', and β-gal monomers.

The recombinant phage, λβ-gal, grown on su⁺ *E. coli* hosts formed blue plaques on agar plate containing the color indicator X-gal, indicating that active β-gal had been made. However, β-gal activity does not conclusively demonstrate that β-gal was incorporated onto the surface of the phage particles. Phage particles were therefore purified to eliminate β-gal proteins that were not incorporated into the surface of phage particles.

3) Preparation of Phage Particles Displaying β-gal Multimer

Phage particles grown on EQ166 (su⁻) and MC8 (su⁺) were produced and purified for further experiments which demonstrate that β-gal had been incorporated onto the surface of the phage particles. Growth in a su⁺ *E. coli* strain MC8 produced the pV'-β-gal fusion protein, pV', and wild-type β-gal monomers. These proteins were either assembled into the phage particles to form functionally active pV'-β-gal on the surface of the phage particles or were separate from the phage particles in the culture. The purification step was necessary to separate the phage particles containing the functionally active pV'-β-gal fusion protein from the remaining proteins in the culture.

One of skill in the art would realize the wild-type β-gal would need to be provided in some manner in order to form the functionally active β-gal tetrameric complex and that the wild-type β-gal monomer may be provided in cis or in trans. The conditional suppression method of expression, of this invention, is one example of providing the wild-type β-gal monomer in cis.

4) Immunoblotting of Phage Particles Displaying β-gal Multimer

The incorporation of the pV'-β-gal fusion protein into phage particles was also detected by analysis of proteins on a polyacrylamide-SDS gel stained with PAGE blue 83 (BDH, Poole, England) and immunoblotted with an α-β-gal antibody. Phage particles from the λfoo vector without insert and λβ-gal were produced in MC8 (su$^+$) and EQ166 (su$^-$) as described in Example 2a2 above.

Phage proteins were dissociated by boiling in a sample buffer (63 mM tris-Cl, pH 6.8; 10% (v/v) glycerol, 1% (w/v) SDS, 1% (v/v) β-mercaptoethanol, 0.0005% Bromophenol blue). Phage proteins were further analyzed by standard methods as described in *Molecular Cloning: A Laboratory Manual, Second Edition*, Maniatis et al., eds., Cold Spring Harbor, N.Y., 1989). Phage proteins were separated by 10% SDS-polyacrylamide gel electrophoresis (PAGE). After electrophoresis, viral proteins in the SDS-PAGE gel were either stained with PAGE blue 83 or electrophoretically transferred onto a nitrocellulose membrane at 300 amps for 15 hours in a cold room to generate a nitrocellulose blot. Nitrocellulose blots of viral proteins were preblocked by washing four times in a blocking buffer (1× phosphate-buffered saline [PBS] containing 5% [w/v] nonfat dry milk, 0.1% [v/v] Nonidet P-40, and 0.05% [w/v] sodium azide) at room temperature for 30 minutes. The blots were then incubated with a primary antibody, the mouse monoclonal anti-β-gal, at 5 µg/ml (Promega, Madison, Wis.) at room temperature for 30 minutes. After washing three times with the blocking buffer, the filter was incubated with a secondary antibody, goat anti-mouse IgG, conjugated with alkaline phosphatase (Promega, Madison, Wis.). After removing unbound antibodies by washing as described above, the alkaline phosphatase conjugated antibody bound to the β-gal on the filter was reacted with nitro blue tetrazolium (NET) at a concentration of 50 µg/ml in 70% dimethylformamide (DMF) and 5-bromo-4-chloro-3-indolyl phosphate (BCIP) at a concentration of 50 µg/ml in 70% DMF to form an insoluble blue precipitate on the filter. The color development was stopped by rinsing the filter twice in deionized water.

Three phage proteins were produced with λβ-gal and λfoo in EQ166 (su$^-$) and MC8 (su$^+$), respectively, as visualized in the PAGE blue 83 stained gel (FIG. 3). Four phage proteins were produced with λβ-gal in the *E. coli* host MC8 (su$^+$). Two of the four phage proteins produced with λβ-gal in MC8 (su$^+$) react with the β-gal antibody. The two proteins represent the fusion protein (pV'-β-gal) and the β-gal monomeric proteins which were incorporated into the surface of the bacteriophage particle. No proteins which were recognized with the β-gal antibody were detected in either the λβ-gal or λfoo in EQ166 and MC8, respectively. λβ-gal expresses only β-gal monomers in the su$^-$ strain EQ166 and does not express the fusion protein (pV'-β-gal) which would be incorporated onto the surface of the phage particle and assemble with β-gal monomers. λfoo does not contain a β-gal gene and therefore does not express β-gal proteins.

5) β-gal Activity Assay with Phage Particles Displaying β-gal Multimer

A comparison of β-gal activity associated with phage particles expressed from λβ-gal and λfoo in the EQ166 (su$^-$) and MC8 (su$^+$) *E. coli* strains was made. Phage particles of λβ-gal and λfoo grown on EQ166 (su$^-$) and MC8 (su$^+$) were purified by ultracentrifugation in Example 2a3. β-gal activity of the purified phage particles was measured according to methods described by Miller (*A Short Course in Bacterial Genetics*, Cold Spring Harbor Lab. Press, Plainview, N.Y., 1992). λβ-gal phage particles prepared from the culture grown on EQ166 (su$^-$) had only residual β-gal activity compared to that of λfoo. However, λβ-gal phage particles prepared in MC8 (su$^+$) had substantial activities when compared to λfoo. λβ-gal phage particles expressed in EQ166 (su$^-$) had 3% of the β-gal activity of phage particles expressed in MC8 (su$^+$). These results indicate that both the pV'-β-gal fusion protein and wild-type β-gal monomers were expressed from λβ-gal in MC8 (su$^+$). They also indicate that the pV'-β-gal fusion protein was incorporated into the phage particles and that the wild-type β-gal monomers had assembled with pV'-β-gal on the surface of the phage particles to form a functionally active β-gal tetramer.

6) Electron Microscopy of Phage Particles Displaying β-gal Multimer

The presence of β-gal multimers on the surface of phage particles was visualized in electron microscopy. β-gal phage particles were produced in Q358 (su$^+$) in liquid culture and purified by centrifugation through a CsCl gradient as described in Example 2a3. Phage were negatively stained with uranyl acetate and visualized at a magnification of 60,200×. Among about 700 phages analyzed by electron microscopy, derived from two separate phage preparations, 55% of phage have no β-gal on the surface, 41% have one β-gal molecule, 3% have two β-gal molecules, and only 1% have three or more β-gal molecules. These results indicate that more than two molecules on a phage on a virion particle may have an inhibitory effect on the tail assembly and explain the poor growth of fusion phage particles on hosts with strong suppressor activity.

7) Affinity Selection of Phage Particles Displaying β-gal Multimer

Affinity selection of phage particles displaying the β-gal multimer by a modified enzyme-linked immunosorbent assay (ELISA) was essentially as described by Engvall et al., *Immunochemistry*, 8:871-879, 1971. The input ratio of phage particles produced by λβ-gal and λV'sac was varied and the output ratio determined by the color screening method using X-gal as described in Example 2a2. Enrichment of phage particles produced by λβ-gal over λV'sac was determined by a comparison of the input to output phage (Table 1).

Microtiter wells (Dynatech, Chantilly, Va.) were coated with 5 µg/ml mouse monoclonal anti-β-gal antibody in coating buffer (0.1 M carbonate buffer, pH 9.6) at 4° C. overnight. Unbound antibody was removed by washing twice with a blocking buffer (1× phosphate buffered saline (PBS) with 0.1% (v/v) Tween 20, 0.25% (w/v) bovine serum albumin (BSA), 5% (w/v) skimmed milk, and 0.1% (w/v) sodium azide). Nonspecific binding sites in the wells were blocked with the blocking buffer at room temperature for one hour, washed twice with λ-dil (10 mM tris-Cl, pH 7.4, 5 mM MgCl$_2$, 0.2 M NaCl, 0.1% (w/v) gelatin). Then 50 µl of a mixture of λβ-gal and λV'sac phage in λ-dil was added to the wells and incubated at room temperature for one hour.

Unbound phage were removed by washing with a washing solution (1×PBS, 5% (w/v) skimmed milk, and 0.5% (v/v) Tween 20) at 37° C. for 30 minutes. Non-specifically bound phage were eluted with elution buffer (10 mM tris-Cl, pH 7.4, 5 mM MgSO$_4$, 0.2 M NaCl, 10 mM CaCl$_2$) at 37° C. for 30 minutes. Specifically bound phage were eluted from the wells with 20 units of collagenase in a elution buffer at 37° C. for 30 minutes. Eluates were assayed for infectivity of EQ166 by adding 0.1 ml of overnight culture of the bacterium in CY medium (1.0 g casamino acids, 5 g yeast extract, 3 gm NaCl, 2 g KCl in 1 liter of distilled water, pH 7.0) supplemented with 5 mM MgSO$_4$ and incubated at 37° C. for 15' minutes. The infected bacteria were plated as previously described in Example 2a2 with X-gal. The numbers of blue and colorless plaques representing λβ-gal and λV'sac, respectively, were determined (Table 1). The enrichment of phage produced by λβ-gal to λV'sac was determined by comparing the numbers of input to output phage particles.

TABLE 1

| Input phage λβ-gal/λV' sac | Output Phage λβ-gal/λV' sac | Enrichment |
|---|---|---|
| $10^4/10^{10}$ | 129/162 | $7.7 \times 10^5$ |
| $10^4/10^9$ | 108/39 | $3.0 \times 10^5$ |
| $10^4/10^8$ | 168/25 | $1.7 \times 10^5$ |
| $10^4/10^7$ | 96/6 | $1.6 \times 10^4$ |
| $10^3/10^{10}$ | 5/106 | $5.3 \times 10^5$ |
| $10^3/10^9$ | 99/32 | $2.8 \times 10^5$ |
| $10^3/10^8$ | 8/11 | $0.8 \times 10^5$ |
| $10^3/10^7$ | 10/5 | $0.2 \times 10^4$ |
| $10^3/10^6$ | 8/0 | $>8.0 \times 10^3$ |

Microtiter plates coated with anti-β-gal antibodies were used to demonstrate the efficiency with which the fusion phage, λβ-gal, can be purified by affinity chromatography. A mixture of λβ-gal and λV'sac phage grown on MC8 (su$^+$) in liquid culture were subjected to a single round of affinity selection. As shown above in Table 1, a $10^4$- to $10^6$-fold enrichment of λβ-gal phage over the reference phage λV'sac occurred, using various ratios of input phage. The average efficiency of recovery of the λβ-gal phage was about 1% of the input phage. These efficiencies of enrichment and recovery with λfoo are comparable to those using the filamentous phage vectors (Scott et al., *Science*, 249:386-390, 1990 and McCafferty et al., *Nature*, 348:552-554, 1990).

3. Methods of Producing a Functionally Active BPA Fusion Protein on the Surface of Lambda Phage Particles Another multimeric protein, BPA, was also incorporated onto the surface of phage particles by the same methods described in Example 2 for incorporation of β-gal on to the surface of phage particles by expression in the λfoo vector.

A. Insertion of BPA Gene into λfoo

The λBPA gene was amplified from *B. purpurea* lectin cDNA (Kusui, *J. Biochem.*, 109:899-903, 1991) by PCR with a pair of oligonucleotide primers (5'-GTCTGCAGCA-CAAGCTCAACCTTA-3', SEQ ID NO 7 and 5'-GAGAAT-TCTTTACATACTGGAATAAGAG-3', SEQ ID NO 8). The two primers were designed to obtain the cDNA encoding a mature lectin protein lacking a leader sequence or signal peptide and with a HindIII restriction site at the 5' end and BamHI site at the 3' end. The PCR fragment was directionally inserted into pUC18 (Pharmacia, Piscataway, N.J.) which had been digested with HindIII and BamHI. Vectors containing inserts were identified as white colonies from transformants of *E. coli* TG1 host ([Δ(lac-proAB), supE, thi, hsdD4/F', traD36, proAB, lacI$^q$ZΔM15] on an indicator plate containing the inducer isopropyl-β-D-galactopyranoside (IPTG) and the color substrate X-gal. IPTG induces expression of the BPA gene from the lacZ promoter in the pUC18 vector. X-gal forms a blue color in the presence of β-gal as explained in Example 2a2. Thus, colonies which contain the BPA insert would form white colonies in the presence of IPTG and X-gal. The presence of the BPA insert was confirmed by DNA sequencing (Sanger et al., *J. Mol. Biol.* 162:729, 1982). The cDNA encoding BPA was subsequently transferred into the λfoo vector by directional insertion at the HindIII and BamHI cloning sites and the construct was confirmed by restriction mapping.

B. Expression of pV/BPA Fusion Protein and Incorporation into Phage Particles by Conditional Suppression The expression of recombinant phage containing the BPA insert in λfoo was characterized by conditional suppression in several *E. coli* strains as described in Example 2a2. Growth in a su$^-$ host would express only the pV' protein and the BPA monomeric protein. The pV'-BPA fusion protein consisting of the pV', linker peptide, and BPA monomer would not be expressed. The fusion protein would not be expressed because a tRNA which can insert an amino acid at the amber codon in the pV coding sequence is not present in a su$^-$ host. The pV protein would therefore be truncated at the amber codon present at amino acid residue 177 of the pV protein. The monomeric BPA protein would be expressed from the ribosome binding site and methionine start codon contained within the coding sequence of the Pro-Thr linker. The monomeric BPA protein is encoded by the DNA insert in the λ vector. Thus, although the BPA monomers expressed from the ribosome binding site in the Pro-Thr linker peptide would assemble to form a BPA multimeric complex with enzymatic activity, the BPA multimeric complex would not be incorporated into phage particles by means of the pV-BPA fusion protein.

Growth in a su$^+$ host would express the pV', pV-BPA fusion protein, and BPA monomeric proteins from the tricistronic message. The pV-BPA fusion protein, consisting of pV', the Pro-Thr linker peptide, and monomeric BPA would be incorporated into the phage particle by means of the pV' matrix anchor. Monomeric BPA expressed from the ribosome binding site and start codon in the Pro-Thr linker sequence would also be expressed and assemble with the pV-BPA fusion protein to form a enzymatically active BPA on the surface of the phage particles.

C. Preparation of Phage Particles Displaying BPA Multimer

Phage particles grown on the MC8 (su$^+$) strain were produced and purified as described in Example 2a2 for affinity selection experiments which demonstrate that BPA had been incorporated onto the surface of the phage particles. Growth in a su$^+$ *E. coli* strain MC8 produced the pV'-BPA fusion protein, pV', and wild-type BPA monomers. These proteins were either assembled into the phage particles to form functionally active pV'-BPA on the surface of the phage particles or were separate from the phage particles in the culture. The purification step was necessary to separate the phage particles containing the functionally active pV'-BPA fusion protein from the remaining proteins in the culture.

Phage particles grown on the MC8 (su$^+$) strain were produced and partially purified for competitive ELISA experiments which demonstrate that binding of BPA to mucin is competitively inhibited in the presence of known antagonists. Growth in a su$^+$ *E. coli* strain MC8 produced the pV'-BPA fusion protein, pV', and wild-type BPA monomers. These proteins were either assembled into the phage particles to form functionally active pV'-BPA on the surface of the phage particles or were separate from the phage particles in the culture. The purification step was necessary to separate the phage particles containing the functionally active pV'-BPA fusion protein from the remaining proteins in the culture.

λBPA were grown on the MC8 (su$^+$) strain in CY medium and partially purified by precipitation with polyethylene glycol (PEG) with a molecular weight cutoff, $M_r$, of 8000 as described in *Molecular Cloning: A Laboratory Manual, Second Edition*, Maniatis et al., eds., Cold Spring Harbor, N.Y., 1989).

D. Affinity Selection of Phage Particles Displaying BPA Multimer

Phage particles which display the BPA multimer were affinity selected in ELISA assays as described in Example 2a7 for selection of phage particles which display the BPA multimer with the following modifications. Bovine submaxillary glands (mucin, Sigma, St. Louis, Mo.) was used as the ligand and 1 mM $CaCl_2$ was added to the binding and washing buffers. $CaCl_2$ was added to the buffers because BPA binding to mucin is calcium-dependent. λBPA phages were enriched $10^3$- to $10^4$-fold over the reference λV'sac phage in the ELISA assays for affinity selection with about a 0.01% recovery of input phage. The lower enrichment and recovery may be due to the lower association constant of BPA to the mucin compared to that of the β-gal and its antibody.

E. Competitive ELISA to Determine Binding Specificity of Phage Particles Displaying BPA Multimer Phage particles displaying BPA on their surface as prepared in Example 2a2 were then analyzed by competition ELISA to determine the specificity of binding of BPA to various sugars. The competitive ELISA was performed on microtiter wells coated with mucin. Increasing concentrations of soluble or free glucose, maltose, lactose, or galactose from 0.00 to 0.1 M were admixed with $10^{10}$ phage particles displaying BPA on their surface. After incubation and washes as described in Example 2a7, bound phage particles were eluted from the microtiter wells with collagenase as described in Example 2a7. Data presented is the mean of three separate experiments.

Lactose and galactose inhibited the binding of λBPA to mucin by 50% at concentrations of 0.1 to 0.3 M, respectively. Maltose inhibited the binding of λBPA to mucin by 50% at approximately 0.7M. Glucose inhibited the binding of λBPA to mucin by only 20% at 1.0M. These results are consistent with evidence that BPA binds specifically to β-D-galactose residues and especially to Galβ1-3-N-acetylgalactosamine (Osawa et al., *Ann. Rev. Biochem.*, 56:21-42, 1987).

4. Methods of Producing a Library of Biologically Active Fusion Polypeptides on the Surface of Lambda Phage Particles The method for producing and segregating a desired biologically active multimeric complexes can be applied to the identification of a desired biologically active multimeric complex from a population of phage. Said population, or library, of phage contains phage which each display a unique biologically active multimeric complex in a surface accessible manner and contain a genome which encodes the multimeric complex.

The method by which the desired biologically active multimeric complex is segregated from the library and thus is identified has been described herein.

Deposit of Materials

The *E. coli* microorganism, MC8, ATCC Accession Number 69674, and bacteriophage lambda DNA, γfoo, ATCC Accession Number 75850, were deposited on Aug. 4, 1994, with the American Type Culture Collection, 1301 Parklawn Drive, Rockville, Md., USA (ATCC). The deposit provides a microorganism that is capable of infection by, replication of, and expression of the lambdoid expression vectors described in Example 1. The bacteriophage lambda DNA, γfoo, is a lambdoid expression vector of this invention and is described in Example 1.

This deposit was made under the provisions of the Budapest Treaty on the International Recognition of the Deposit of Microorganisms for the Purpose of Patent Procedure and the Regulations thereunder (Budapest Treaty). This assures maintenance of a viable microorganism and bacteriophage lambda DNA for 30 years from the date of deposit. The microorganism and bacteriophage lambda DNA will be made available by ATCC under the terms of the Budapest Treaty which assures permanent and unrestricted availability of the progeny of the culture and DNA to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the culture or DNA deposit should die or be lost or destroyed when cultivated under suitable conditions, it will be promptly replaced on notification with a viable specimen of the same culture or DNA, respectively. Availability of the deposited strain and DNA is not to be construed as a license to practice the invention in contravention of the rights granted under the authority of any government in accordance with its patent laws.

The foregoing is intended as illustrative of the present invention but not limiting. Numerous variations and modifications can be effected without departing from the true spirit and scope of the invention.

---

What is claimed is:

1. A fusion protein having an amino acid residue sequence that comprises, in the direction of amino terminus to carboxy terminus, a lambdoid bacteriophage matrix anchor polypeptide domain operably linked to a preselected polypeptide, wherein the lambdoid bacteriophage matrix anchor polypeptide is head polypeptide pD or tail polypeptide pV.

2. The fusion protein of claim 1, further comprising a linker polypeptide wherein said matrix anchor polypeptide domain is operably linked to said linker polypeptide and said linker polypeptide is operably linked to said preselected poly-peptide.

3. The fusion protein of claim 1, wherein said matrix anchor poly-peptide domain comprises a lambdoid bacteriophage pD head poly-peptide domain.

4. The fusion protein of claim 1, wherein said matrix anchor polypeptide domain comprises a lambdoid bacteriophage pV tail polypeptide domain.

5. The fusion protein of claim 4, wherein said pV tail polypeptide domain comprises residues 1-176 of the amino acid residue sequence shown in SEQ ID NO:1.

6. A recombinant lambdoid bacteriophage vector comprising a nucleotide sequence that (i) defines the lambdoid elements for replication and packaging of the vector into an assembled bacteriophage, and (ii) encodes a conditionally suppressible cistron for expression of a fusion polypeptide, which nucleotide sequence comprises:

a) a promoter for transcribing the cistron,
    b) a first upstream translatable sequence that encodes a lambdoid bacteriophage head protein pD or tail protein pV,
    c) a first ribosome binding site to initiate translation of said upstream translatable sequence,
    d) a second translatable sequence operatively linked downstream to said first translatable sequence that (i) encodes a linker polypeptide in frame with said matrix anchor polypeptide domain and (ii) includes a sequence adapted for ligation of an insert polynucleotide that defines a third translatable sequence downstream from said second translatable sequence that encodes a preselected polypeptide, and e) a suppressor termination codon within said second translatable sequence that upon suppression results in read-through to form the fusion polypeptide comprising lambdoid bacteriophage head protein pD or tail protein pV, said linker polypeptide, and said preselected polypeptide.

7. The vector of claim 6, wherein said second translatable sequence further includes a nucleotide sequence that defines a second ribosome binding site to initiate translation of said third translatable sequence.

8. A recombinant lambdoid bacteriophage comprising a matrix of proteins encapsulating a lambdoid genome encoding a fusion protein, said matrix including said fusion protein, surface accessible in said matrix, and said fusion protein comprising, in the direction of amino terminus to carboxy terminus, a lambdoid bacteriophage head protein pD or tail protein pV operably linked to a preselected polypeptide.

9. The lambdoid bacteriophage of claim 8, wherein said preselected polypeptide defines a biologically active protein selected from the group consisting of an enzyme, a ligand, and a receptor.

10. The lambdoid bacteriophage of claim 8, further comprising a linker polypeptide wherein said head protein pD or tail protein pV is operably linked to said linker polypeptide and said linker polypeptide is operably linked to said preselected polypeptide.

11. The lambdoid bacteriophage of claim 8, wherein said fusion protein comprises a lambdoid bacteriophage head polypeptide pD.

12. The lambdoid bacteriophage of claim 8, wherein said fusion protein comprises a lambdoid bacteriophage tail polypeptide pV.

13. The lambdoid bacteriophage of claim 8, wherein said lambdoid genome further encodes a heterologous protein capable of forming a multimeric protein complex with said fusion protein in said matrix.

14. The lambdoid bacteriophage of claim 8, wherein said fusion protein is present as a multimeric protein.

15. The lambdoid bacteriophage of claim 14, wherein said multimeric protein is selected from the group consisting of beta-galactosidase and *Bauhinia purpurea* agglutinin.

16. The lambdoid bacteriophage of claim 10, wherein said linker polypeptide has an amino acid residue sequence form 178 to 213 as shown in SEQ ID NO:6.

17. The lambdoid bacteriophage of claim 8, wherein said bacteriophage is detectably labeled.

18. A library of recombinant lambdoid bacteriophage particles wherein each particle contains a recombinant lambdoid bacteriophage vector according to claim 6.

19. The library of claim 18, wherein said library contains at least $10^7$ different species of said vector.

20. A method for detecting the presence of a preselected target in a sample comprising the steps of:
a) admixing a sample containing said preselected target with a recombinant lambdoid bacteriophage according to claim 8, wherein said preselected polypeptide defines a biologically active ligand or receptor able to bind said preselected target, under binding conditions sufficient for said target-binding bacteriophage to bind said target and form a target-ligand or receptor complex; and
b) detecting the presence of said complex, and thereby the presence of said preselected target.

21. The method of claim 20, wherein said detecting comprises detecting the presence of said bacteriophage particles, and thereby the presence of said preselected target.

22. A method for producing a recombinant lambdoid bacteriophage, comprising the steps of:
a) infecting an *E. coli* host strain having a termination codon suppression phenotype with a recombinant lambdoid bacteriophage vector according to claim 6; and
b) culturing said infected host strain under bacteriophage growth conditions to produce said recombinant lambdoid bacteriophage.

23. The method of claim 22, wherein said *E. coli* host strain is selected from the group consisting of EQ166, CA168, and MC8.

24. The method of claim 22, wherein said *E. coli* host strain is MC8 and has the characteristics of ATCC accession number 69674.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 246 amino acids
      (B) TYPE: amino acid
      (C) STRANDEDNESS: single (D) TOPOLOGY: linear (ii) MOLECULE TYPE: <Unknown>

(xi) SEQUENCE DESCRIPTION: SEQ ID NO: 1:

Met Pro Val Pro Asn Pro Thr Met Pro Val Lys Gly Ala Gly Thr Thr
1               5                   10                  15

Leu Trp Val Tyr Lys Gly Ser Gly Asp Pro Tyr Ala Asn Pro Leu Ser
            20                  25                  30

Asp Val Asp Trp Ser Arg Leu Ala Lys Val Lys Asp Leu Thr Pro Gly
        35                  40                  45

Glu Leu Thr Ala Glu Ser Tyr Asp Asp Ser Tyr Leu Asp Asp Glu Asp
    50                  55                  60

Ala Asp Trp Thr Ala Thr Gly Gln Gly Gln Lys Ser Ala Gly Asp Thr
65                  70                  75                  80

Ser Phe Thr Leu Ala Trp Met Pro Gly Glu Gln Gly Gln Gln Ala Leu
                85                  90                  95

Leu Ala Trp Phe Asn Glu Gly Asp Thr Arg Ala Tyr Lys Ile Arg Phe
            100                 105                 110

Pro Asn Gly Thr Val Asp Val Phe Arg Gly Trp Val Ser Ser Ile Gly
        115                 120                 125

Lys Ala Val Thr Ala Lys Glu Val Ile Thr Arg Thr Val Lys Val Thr
130                 135                 140

Asn Val Gly Arg Pro Ser Met Ala Glu Asp Arg Ser Thr Val Thr Ala
145                 150                 155                 160

Ala Thr Gly Met Thr Val Thr Pro Ala Ser Thr Ser Val Val Lys Gly
                165                 170                 175

Gln Ser Thr Thr Leu Thr Val Ala Phe Gln Pro Glu Gly Val Thr Asp
            180                 185                 190

Lys Ser Phe Arg Ala Val Ser Ala Asp Lys Thr Lys Ala Thr Val Ser
        195                 200                 205

Val Ser Gly Met Thr Ile Thr Val Asn Gly Val Ala Ala Gly Lys Val
210                 215                 220

Asn Ile Pro Val Val Ser Gly Asn Gly Glu Phe Ala Ala Val Ala Glu
225                 230                 235                 240

Ile Thr Val Thr Ala Ser
                245

(2) INFORMATION FOR SEQ ID NO: 2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

AGTGTGGAGC TCTACCCTTT C                                                    21

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

CGCCTGTAAT AAGCGGCCGC AGCT                                          24

(2) INFORMATION FOR SEQ ID NO: 4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GCGGCCGCTT ATTACAGG                                                 18

(2) INFORMATION FOR SEQ ID NO: 5:

(i) SEQUENCE CHARACTERISTICS:
        (A) LENGTH: 910 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

AAATGTGAGG ACGCTATGCC TGTACCAAAT CCTACAATGC CGGTGAAAGG              50

TGCCGGGACC ACCCTGTGGG TTTATAAGGG GAGCGGTGAC CCTTACGCGA             100

ATCCGCTTTC AGACGTTGAC TGGTCGCGTC TGGCAAAAGT TAAAGACCTG             150

ACGCCCGGCG AACTGACCGC TGAGTCCTAT GACGACAGCT ATCTCGATGA             200

TGAAGATGCA GACTGGACTG CGACCGGGCA GGGGCAGAAA TCTGCCGGAG             250

ATACCAGCTT CACGCTGGCG TGGATGCCCG GAGAGCAGGG GCAGCAGGCG             300

CTGCTGGCGT GGTTTAATGA AGGCGATACC CGTGCCTATA AAATCCGCTT             350

CCCGAACGGC ACGGTCGATG TGTTCCGTGG CTGGGTCAGC AGTATCGGTA             400

AGGCGGTGAC GGCGAAGGAA GTGATCACCC GCACGGTGAA AGTCACCAAT             450

GTGGGACGTC CGTCGATGGC AGAAGATCGC AGCACGGTAA CAGCGGCAAC             500

CGGCATGACC GTGACGCCTG CCAGCACCTC GGTGGTGAAA GGGTAGAGCT             550

GGCCTGTTAG GCCCACTCCG ACCCCGACCA CTCCCACCCC GACTCCCACC             600

CCGACCCCGA CCCCGACTCC GACCGTTGGG CCAATTGTCA CACAGGAAAC             650

AGCTATGACC ATGATTACGC CAAGCTTGCA TGCCTGCAGG TCGACTCTAG             700

AGGATCCCCG GGTACCGAGC TCGAATTCAC TGGCCGTCGT TTTACAACGT             750

CGTGACTGGG AAAACCCTGG CGTTACCCAA CTTAATCGCC TTGCAGCACA             800

TCCCCCTTTC GCCAGCTGGC GTAATAGCGA AGAGGCCCGC ACCGATCGCC             850

CTTCCCAACA GTTGCGCAGC CTGAATGGCG AATGGCGCCT GTAATAAGCG             900

GCCGCAGCTC                                                        910

(2) INFORMATION FOR SEQ ID NO: 6:

(i) SEQUENCE CHARACTERISTICS:
        (A) LENGTH: 292 amino acids
        (B) TYPE: amino acid
        (D) TOPOLOGY: linear

```
    (ii) MOLECULE TYPE: protein (ix) FEATURE:
         (A) NAME/KEY: peptide
         (B) LOCATION: 177
         (D) OTHER INFORMATION: /label= Xaa
             /note= "Wherein Xaa is a suppressor termination
             codon"

(xi) SEQUENCE DESCRIPTION: SEQ ID NO: 6:

Met Pro Val Pro Asn Pro Thr Met Pro Val Lys Gly Ala Gly Thr Thr
 1               5                  10                  15

Leu Trp Val Tyr Lys Gly Ser Gly Asp Pro Tyr Ala Asn Pro Leu Ser
                20                  25                  30

Asp Val Asp Trp Ser Arg Leu Ala Lys Val Lys Asp Leu Thr Pro Gly
             35                  40                  45

Glu Leu Thr Ala Glu Ser Tyr Asp Asp Ser Tyr Leu Asp Asp Glu Asp
         50                  55                  60

Ala Asp Trp Thr Ala Thr Gly Gln Gly Gln Lys Ser Ala Gly Asp Thr
65                  70                  75                  80

Ser Phe Thr Leu Ala Trp Met Pro Gly Glu Gln Gly Gln Gln Ala Leu
                 85                  90                  95

Leu Ala Trp Phe Asn Glu Gly Asp Thr Arg Ala Tyr Lys Ile Arg Phe
            100                 105                 110

Pro Asn Gly Thr Val Asp Val Phe Arg Gly Trp Val Ser Ser Ile Gly
        115                 120                 125

Lys Ala Val Thr Ala Lys Glu Val Ile Thr Arg Thr Val Lys Val Thr
130                 135                 140

Asn Val Gly Arg Pro Ser Met Ala Glu Asp Arg Ser Thr Val Thr Ala
145                 150                 155                 160

Ala Thr Gly Met Thr Val Thr Pro Ala Ser Thr Ser Val Val Lys Gly
                165                 170                 175

Xaa Ser Trp Pro Val Arg Pro Thr Pro Thr Pro Thr Thr Pro Thr Pro
            180                 185                 190

Thr Pro Thr Pro Thr Pro Thr Pro Thr Pro Thr Val Gly Pro Ile Val
        195                 200                 205

Thr Gln Glu Thr Ala Met Thr Met Ile Thr Pro Ser Leu His Ala Cys
210                 215                 220

Arg Ser Thr Leu Glu Asp Pro Arg Val Pro Ser Ser Asn Ser Leu Ala
225                 230                 235                 240

Val Val Leu Gln Arg Arg Asp Trp Glu Asn Pro Gly Val Thr Gln Leu
                245                 250                 255

Asn Arg Leu Ala Ala His Pro Pro Phe Ala Ser Trp Arg Asn Ser Glu
            260                 265                 270

Glu Ala Arg Thr Asp Arg Pro Ser Gln Gln Leu Arg Ser Leu Asn Gly
        275                 280                 285

Glu Trp Arg Leu
290

(2) INFORMATION FOR SEQ ID NO: 7:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)
```

```
        (xi) SEQUENCE DESCRIPTION: SEQ ID NO: 7:

GTCTGCAGCA CAAGCTCAAC CTTA                                          24

(2) INFORMATION FOR SEQ ID NO: 8:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 8:

GAGAATTCTT TACATACTGG AATAAGAG                                      28

(2) INFORMATION FOR SEQ ID NO: 9:

(i) SEQUENCE CHARACTERISTICS:
         (A) LENGTH: 4 amino acids
         (B) TYPE: amino acid
         (D) TOPOLOGY: linear (ii) MOLECULE TYPE: protein (xi) SEQUENCE DESCRIPTION: SEQ ID NO: 9:

Val Val Lys Gly
 1

(2) INFORMATION FOR SEQ ID NO: 10:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 10:

GTGGTGAAAG GGTAGAGCTC CACACTG                                       27

(2) INFORMATION FOR SEQ ID NO: 11:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 11:

CAGTGTGGAG CTCTACCCTT TCACCAC                                       27

(2) INFORMATION FOR SEQ ID NO: 12:

(i) SEQUENCE CHARACTERISTICS:
         (A) LENGTH: 12 amino acids
         (B) TYPE: amino acid
         (D) TOPOLOGY: linear (ii) MOLECULE TYPE: protein (xi) SEQUENCE DESCRIPTION: SEQ ID NO: 12:

Ser Ser Ser Leu Asp Pro Gly Pro Ser Thr Asn Ser
 1               5                  10
```

(2) INFORMATION FOR SEQ ID NO: 13:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
GGGTAGAGCT CAAGCTTGGA TCCGGGCCCG TCGACGAATT C          41
```

(2) INFORMATION FOR SEQ ID NO: 14:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO: 14:

```
Ser Trp Pro Val Gly Pro Ile Val Thr Gln Glu Thr Ala Met Thr Met
1               5                   10                  15

Ile Thr Pro Ser Leu His Ala Cys Arg Ser Thr Leu Glu Asp Pro Arg
            20                  25                  30

Val Pro Ser Ser Asn Ser
        35
```

(2) INFORMATION FOR SEQ ID NO: 15:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
GGGTAGAGCT GGCCTGTTGG GCCAATTGTC ACACAGGAAA CAGCTATGAC CATGATTACG     60
CCAAGCTTGC ATGCCTGCAG GTCGACTCTA GAGGATCCCC GGGTACCGAG CTCGAATTC     119
```